US012698466B2

(12) United States Patent
Du et al.

(10) Patent No.: US 12,698,466 B2
(45) Date of Patent: Aug. 4, 2026

(54) NANOPARTICLES BASED METHOD FOR SCREENING ENZYME OR MICROORGANISM

(71) Applicants: Novozymes A/S, Bagsvaerd (DK); Institute of Microbiology, Chinese Academy of Sciences, Beijing (CN)

(72) Inventors: Wenbing Du, Beijing (CN); Yuxin Qiao, Beijing (CN); Dongwei Chen, Beijing (CN); Shufang Zhao, Beijing (CN); Ming Li, Beijing (CN); Ying Zhang, Beijing (CN); Wanghui Xu, Beijing (CN); Cheng Peng, Beijing (CN); Beiyu Hu, Beijing (CN); Ran Hu, Beijing (CN)

(73) Assignees: Novozymes A/S, Bagsvaerd (DK); Institute of Microbiology, Chinese Academy of Sciences, Beijing (CN)

( * ) Notice: Subject to any disclaimer, the term of this patent is extended or adjusted under 35 U.S.C. 154(b) by 1361 days.

(21) Appl. No.: 17/413,885

(22) PCT Filed: Dec. 12, 2019

(86) PCT No.: PCT/CN2019/124881

§ 371 (c)(1),
(2) Date: Jun. 14, 2021

(87) PCT Pub. No.: WO2020/119766

PCT Pub. Date: Jun. 18, 2020

(65) Prior Publication Data

US 2022/0056387 A1 Feb. 24, 2022

(30) Foreign Application Priority Data

Dec. 14, 2018 (WO) ................ PCT/CN2018/121142

(51) Int. Cl.

| | |
|---|---|
| ***C12M 3/06*** | (2006.01) |
| ***B82Y 5/00*** | (2011.01) |
| ***C12Q 1/37*** | (2006.01) |
| ***C40B 30/08*** | (2006.01) |

(52) U.S. Cl.

CPC ............... *C12M 23/16* (2013.01); *C12Q 1/37* (2013.01); *B82Y 5/00* (2013.01); *C40B 30/08* (2013.01)

(58) Field of Classification Search

None

See application file for complete search history.

(56) References Cited

U.S. PATENT DOCUMENTS

| | | | | |
|---|---|---|---|---|
| 6,255,451 | B1 | 7/2001 | Koch et al. | |
| 2004/0202719 | A1 | 10/2004 | Zion et al. | |
| 2009/0269405 | A1 | 10/2009 | Windsor et al. | |
| 2011/0213121 | A1 | 9/2011 | Kwon et al. | |
| 2013/0243832 | A1 | 9/2013 | Turos et al. | |
| 2014/0255311 | A1 * | 9/2014 | Almutairi et al. ..... | A61K 47/34 514/180 |

FOREIGN PATENT DOCUMENTS

| | | |
|---|---|---|
| KR | 20140024193 | 8/2012 |
| WO | 2003036292 A2 | 5/2003 |

OTHER PUBLICATIONS

Zumstein et al., "High-Throughput Analysis of Enzymatic Hydrolysis of Biodegradable Polyesters by Monitoring Cohydrolysis of a Polyester-Embedded Fluorogenic Probe," Environ. Sci. Technol. 2017, 51:4358-4367. (Year: 2017).*

Hosokawa et al., "Droplet-based microfluidics for high-throughput screening of a metagenomic library for isolation of microbial enzymes," Biosens. Bioelectron. 2015, 67:379-385. (Year: 2015).*

Bunzel et al., "Speeding up enzyme discovery and engineering with ultrahigh-throughput methods," Curr. Opin. Struct. Biol. 2018, 48:149-156, published online Feb. 3, 2018. (Year: 2018).*

Bunzel et al., 2018, Current opinion in structural biology 48, 149-456.

Chaves et al., 2017, Journal of the Brazilian chemical society 29, 1278-1285.

Welzel et al., 2002, Chemie Ingenieur Technik 74, 1496-1500.

Welzel et al., 2002, Chemie Ingenieur Technik 74, 1496-1500—Tr.

Hosokawa et al, 2015, Biosensors and Bioelectronics 67, 379-385.

Zumstein et al, 2017, Environmental Science & Technology 51(8), 4358-4367.

Zumstein, 2017, Env Sci Technol, 1-31.

Zumstein, 2017, Env Sci Technol, 4358-4367.

Chaves et al, 2017, J. Braz. Chem.Soc 29(6), 1278-1285.

* cited by examiner

*Primary Examiner* — Kaijiang Zhang

(74) *Attorney, Agent, or Firm* — Eric J. Fechter

(57) ABSTRACT

A nanoparticle comprises water-insoluble polymer matrix and an indicator constituent(s), wherein the indicator constituent(s) is released from the nanoparticle only when the polymer matrix is degraded or broken, and then an indicative effect is triggered or enhanced. A nanoparticle-based method for screening a bioactive substance and a microfluidic-based screening system have also been disclosed.

14 Claims, 18 Drawing Sheets

FRET peptide sequence: 5-FAM-Ser-His-Leu-Val-Glu-Ala-Leu-Tyr-Lys(Dabcyl)

Molecular Weight: 1668.86

NANOPARTICLES BASED METHOD FOR SCREENING ENZYME OR MICROORGANISM

CROSS-REFERENCE TO RELATED APPLICATIONS

This application is a 35 U.S.C. 371 national application of PCT/CN2019/124881, filed Dec. 12, 2019, which claims priority or the benefit from PCT Application Serial No. PCT/CN2018/121142, filed Dec. 14, 2018. The contents of these applications are fully incorporated herein by reference.

FIELD OF THE INVENTION

The present invention relates to polymer nanoparticles containing an indicator constituent(s), such nanoparticles can be used for screening polymer degrading enzyme or degrading microorganism.

BACKGROUND OF THE INVENTION

There are abundant microbial species in the natural environment, which can degrade polymers such as plastics. Recent studies have found that bacteria, fungi and actinomycetes are the main plastic decomposers in nature.

A simulated substrate that produces fluorescence by enzymatic hydrolysis is commonly used in a highly sensitive screening system. Based on this, a microfluidic chip technology can realize the precise control and analysis of single cells, making it possible to simultaneously detect, separate and extract specific cell individuals from population cells with automation, high throughput, and multiple parameters.

The fluorescence activated droplet sorting (FADS) technology has been published since 2009. The recently emerged single cell sorting technology based on droplet microfluidics technology can accurately package individual cells in droplets, and perform complicated automatic flow operations such as incubation, coalescence, sorting, etc., providing a new idea for developing innovative strain screening equipment with high throughput and low cost. In recent years, scientists in the United States, France and other countries have reported on the FADS sorting of β-galactosidase, horseradish peroxidase, cellulase, α-amylase and fructose diphosphate.

However, because PET and other plastics are water-insoluble polymers, it is very difficult to find a soluble micro molecule monomer as a fluorescence simulated substrate which could well match the properties of the polymer. And due to the different structures of different polymers, it is more difficult to develop a commonly used simulation substrate.

With the rapid development of nanotechnology, functional fluorescent nano-materials with excellent characteristics are continuously emerging, compared with the traditional fluorescent probe, fluorescent nano-materials have the advantages of high optical stability, easy control of shape and size, multifunction and now have been widely used in the fields of biology, chemistry, and medicine.

Therefore, it is urgent to develop a nano-materials based screening method with high throughput and low cost to improve the efficiency of screening microbial resources or biological enzymes that degrade different kinds of polymers.

SUMMARY OF THE INVENTION

The inventors of the present invention have found that water-insoluble polymer nanoparticles containing an indicator constituent(s) can be used for screening an enzyme or a degrading microorganism which is capable of degrading such polymer. When the water-insoluble polymer is degraded or broken, the indicator constituent, such as fluorescent substrate, can be released, and be directly or indirectly excited to fluoresce. Based on this, different screening systems based on polymer nano-materials for microbial resources or biological enzymes capable of degrading different kinds of polymers can be developed, for an instance, nanoparticles based fluorescent activated droplets sorting system.

The present invention relates to a nanoparticle comprising water-insoluble polymer matrix and an indicator constituent(s), wherein the indicator constituent(s) is released from the nanoparticle only when the polymer matrix is degraded or broken, preferably, wherein the indicator constituent is encapsulated in the water-insoluble polymer matrix.

In general, the amount of the indicator constituent encapsulated in the said nanoparticles of the present invention is sufficient to screen a bioactive substance of a library which is capable of degrading or assisting in degrading water-insoluble polymers.

In a preferred embodiment, the mass concentration of the water-insoluble polymer matrix is about 50-99.99%, preferably, about 80-99.99%, such as, about 90-99.99%, more preferably, about 95-99.99%, and the mass concentration of the indicator constituent is about 0.01-50%, preferably, about 0.01-20%, such as about 0.01-10%, more preferably, about 0.01-5%. In a preferred embodiment, when the said water-insoluble polymer matrix is degraded or broken, from which the indicator constituent can be released, and then an indicative effect is triggered or enhanced.

In a preferred embodiment, wherein the said water-insoluble polymer matrix comprises or consists of an enzyme substrate, preferably, the water-insoluble polymer is selected from polyester, starch, saccharides, lipids, lignin, protein, nucleic acid, amylose, cellulose, pectin, chitin, fatty acids, lignin, alginate acid, hyaluronic acid, agar, mannan, xanthan gum, arabic gum, protein, DNA or RNA, preferably, the polyester is, for example, polybutylene terephthalate (PBT), polypropylene terephthalate (PTT), polyethylene terephthalate (PEN), polyethylene terephthalate, tetramethylene terephthalate (PTMT), polyethylene-4-oxybenzoate, polyethylene glycol, polyvinyl chloride, polyglycolic acid, polylactic acid, polyanhydride, polycaprolactone, polyacrylonitrile, polypropylene, polyvinyl alcohol.

In a preferred embodiment, wherein the said indicator constituent is a fluorogenic indicator or chromonic indicator, for example, a fluorogenic or chromonic indicator conjugate having enzyme substrate, preferably, a fluorogenic or chromonic enzyme substrate, wherein the activity of a specific enzyme converts the fluorogenic or chromonic enzyme substrate into an indicative compound, for example, fluorescein.

In a preferred embodiment, wherein both the said polymer matrix and the said indicator constituent have similar or same enzymatic hydrolysis group, preferably, both the polymer matrix and indicator constituent can be both degraded or hydrolyzed by a specific active enzyme, and then, an indicative effect, such as a fluorescence indicative effect, is triggered or enhanced.

The present invention also relates to a microreactor comprising the nanoparticles of the present invention and at least one biologically active substance screening which is capable of degrading or assisting in degrading water-insoluble polymers, preferably, the microreactor is in the form of an aqueous phase, for example in the form of a water droplet, which can be dispersed in the oil phase, or in the form of an oil water droplet, which can be dispersed in the water phase. In a preferred embodiment, the said microreactor has an average diameter of about 1 to 200 microns, preferably 2 to 100 microns, more preferably 10 to 50 microns, more preferably 10 to 30 microns, for example 15 to 25 microns.

In a preferred embodiment, wherein the said bioactive substance is a water-insoluble polymer degrading enzyme or a water-insoluble polymer degrading microorganism, the water-insoluble polymer degrading microorganism is preferably capable of expressing a water-insoluble polymer degrading enzyme or capable of expressing an enhancer of water-insoluble polymer degrading enzyme, optionally, the water-insoluble polymer degrading microorganism is a natural or recombinant cell comprising a polynucleotide of an enzyme of interest.

In a preferred embodiment, wherein the said water-insoluble polymer degrading enzyme is a hydrolase, isomerase, ligase, lyase, oxidoreductase, or transferase, preferably, is an alpha-galactosidase, alpha-glucosidase, aminopeptidase, amylase, asparaginase, beta-galactosidase, beta-glucosidase, beta-xylosidase, sugar enzyme, carboxypeptidase, catalase, cellobiohydrolase, cellulase, chitin enzyme, cutinase, lipolytic enzyme, peroxidase, cyclase, cyclodextrin glycosyltransferase, deoxyribonuclease, endoglucanase, esterase, dextran transferase, glucoamylase, invertase, laccase, lipase, mannosidase, mutase, oxidase, pectin lyase, peroxidase, phytase, polyphenol oxidase, proteolytic enzyme, ribonuclease, transglutaminase, xylanase, PET degrading enzyme or horseradish peroxidase.

The present invention also relates to a kit comprising the nanoparticles of the present invention.

The present invention also relates to a method for screening a bioactive substance of a library which is capable of degrading or assisting in degrading water-insoluble polymers, comprising the steps of:

a) provide nanoparticles of the present invention;
b) contact the bioactive substance to be analyzed with the nanoparticles of the present invention to form a mixture;
c) when an indicative effect, preferably, a fluorescent indicative effect, produced by the indicator constituent, is triggered or enhanced, it indicates that the biologically active substance can degrade or assist in degrading the water-insoluble polymer matrix constituting the nanoparticles.

In a preferred embodiment, wherein the amount of the said indicative effect reaches or is above a predetermined threshold level.

In a preferred embodiment, wherein the said bioactive substance is a water-insoluble polymer degrading enzyme or a water-insoluble polymer degrading microorganism, the water-insoluble polymer degrading microorganism is preferably capable of expressing a water-insoluble polymer degrading enzyme or capable of expressing an enhancer of a water-insoluble polymer degrading enzyme.

In a preferred embodiment, wherein the said library is an enzyme library or a or microorganism library, comprising a multitude of different enzymes or microorganism, wherein the amount of indicative effect released by one enzyme or a microorganism reaches or is above the predetermined threshold level, whereby a targeted enzyme or a targeted microorganism is identified.

In a preferred embodiment, wherein the said library is an enzyme library comprising a multitude of enzyme variants derived from a parent enzyme, wherein an increased amount of indicative effect has been released by the active enzyme variant, as compared with the parent enzyme, whereby an improved enzyme variant is identified.

In a preferred embodiment, wherein the said water-insoluble polymer degrading enzyme is a hydrolase, isomerase, ligase, lyase, oxidoreductase, or transferase, preferably, is an alpha-galactosidase, alpha-glucosidase, aminopeptidase, amylase, asparaginase, beta-galactosidase, beta-glucosidase, beta-xylosidase, sugar enzyme, carboxypeptidase, catalase, cellobiohydrolase, cellulase, chitin enzyme, cutinase, lipolytic enzyme, peroxidase, cyclase, cyclodextrin glycosyltransferase, deoxyribonuclease, endoglucanase, esterase, dextran transferase, glucoamylase, invertase, laccase, lipase, mannosidase, mutase, oxidase, pectin lyase, peroxidase, phytase, polyphenol oxidase, proteolytic enzyme, ribonuclease, transglutaminase, xylanase, PET degrading enzyme or horseradish peroxidase.

The present invention also relates to an enzyme screening or selection method, comprising the steps of:

a) providing an enzyme library and a multitude of compartments, each compartment comprising an aliquot of liquid and at least one solid composition comprising a mixture of an enzyme substrate (preferably about 50-99.99% (w/w)) and the enzyme substrate conjugated to a fluorophore or chromophore marker (preferably about 50-0.01% (w/w));
b) contacting the solid composition in each compartment with an enzyme of the library, wherein both the substrate and substrate-marker conjugate are degraded by an active enzyme, thereby releasing the fluorophore or chromophore marker;
c) identifying one or more compartment, wherein the fluorophore or chromophore marker has been released by the active enzyme, thereby identifying the active enzyme.

In a preferred embodiment, wherein the said enzyme library comprises a multitude of enzyme variants derived from a parent enzyme, and wherein a compartment is identified in step (c), wherein an increased amount of marker has been released by the active enzyme variant, as compared with the parent enzyme, whereby an improved enzyme variant is identified.

In a preferred embodiment, wherein the said solid composition of the comprises or consists of the nanoparticles of the present invention.

In a preferred embodiment, wherein the said compartment comprises or consists of the microreactor of the present invention.

In a preferred embodiment, wherein the said enzyme substrate conjugated to a fluorophore or chromophore marker is a fluorogenic indicator or chromonic indicator, for example, a fluorogenic or chromonic indicator conjugate having enzyme substrate, preferably, a fluorogenic or chromonic enzyme substrate, wherein the activity of a specific enzyme converts the fluorogenic or chromonic enzyme substrate into an indicative compound, for example, fluorescein.

The present invention also relates to a method for screening a bioactive substance of a library which is capable of degrading or assisting in degrading the water-insoluble polymer matrix using a microfluidic-based system, comprising:

a) droplet generation process, wherein droplet containing biologically active substances are generated;
b) nanoparticles introducing process, wherein a secondary droplet containing the nanoparticles of the present invention is coalesced with the droplet generated by unit (a);

c) droplets sorting process, wherein the targeted droplets are sorted based on the indicative effect generated by the indicator, and d) analysis and detection process, wherein the sorted targeted droplets are further analyzed to screen the targeted biologically active substance.

The present invention also relates to a method for screening a bioactive substance of a library which is capable of degrading or assisting in degrading the water-insoluble polymer matrix using a microfluidic-based system, comprising:

a) droplet generation process, wherein an aqueous liquid droplet is generated;

b) nanoparticles introducing process, wherein a droplet containing the nanoparticles of the present invention is coalesced with the droplet generated by unit (a);

c) bioactive substance introducing process, wherein a droplet containing the bioactive substance of a library is coalesced with the droplet generated by unit (a);

d) droplets sorting process, wherein the targeted droplets are sorted based on the indicative effect generated by the indicator, and e) analysis and detection process, wherein the sorted targeted droplets are further analyzed to screen the targeted biologically active substance, wherein process b) can be performed simultaneously, before or after and process c), or process a), process b) and process c) can be performed simultaneously.

In a preferred embodiment, wherein, when the indicative effect of the droplet reaches or is above a preset threshold level, the droplet sorting system triggers the selection of the targeted droplet, preferably, the droplet sorting system triggers the deflection of the target droplet toward selection paths.

In a preferred embodiment, wherein the droplet sorting is based on a fluorescence activated droplet sorting technique.

In a preferred embodiment, the screening method further comprises a droplet incubation process, wherein the droplet containing the biologically active substance is incubated.

In a preferred embodiment, wherein the nanoparticles introduction unit or bioactive substance introducing unit is a picoinjection unit wherein a picoliter volume of aqueous liquid solution comprising nanoparticles or bioactive substance solution can be introduced into the droplet.

In a preferred embodiment, wherein each droplet before sorting comprises at most a single cell.

The present invention also relates to use of nanoparticles of the present invention, a microreactor of the present invention, or a kit of the present invention in screening bioactive substances capable of degrading or assisting in degrading water-insoluble polymers.

DETAILED DESCRIPTION OF THE INVENTION

Figure 1:
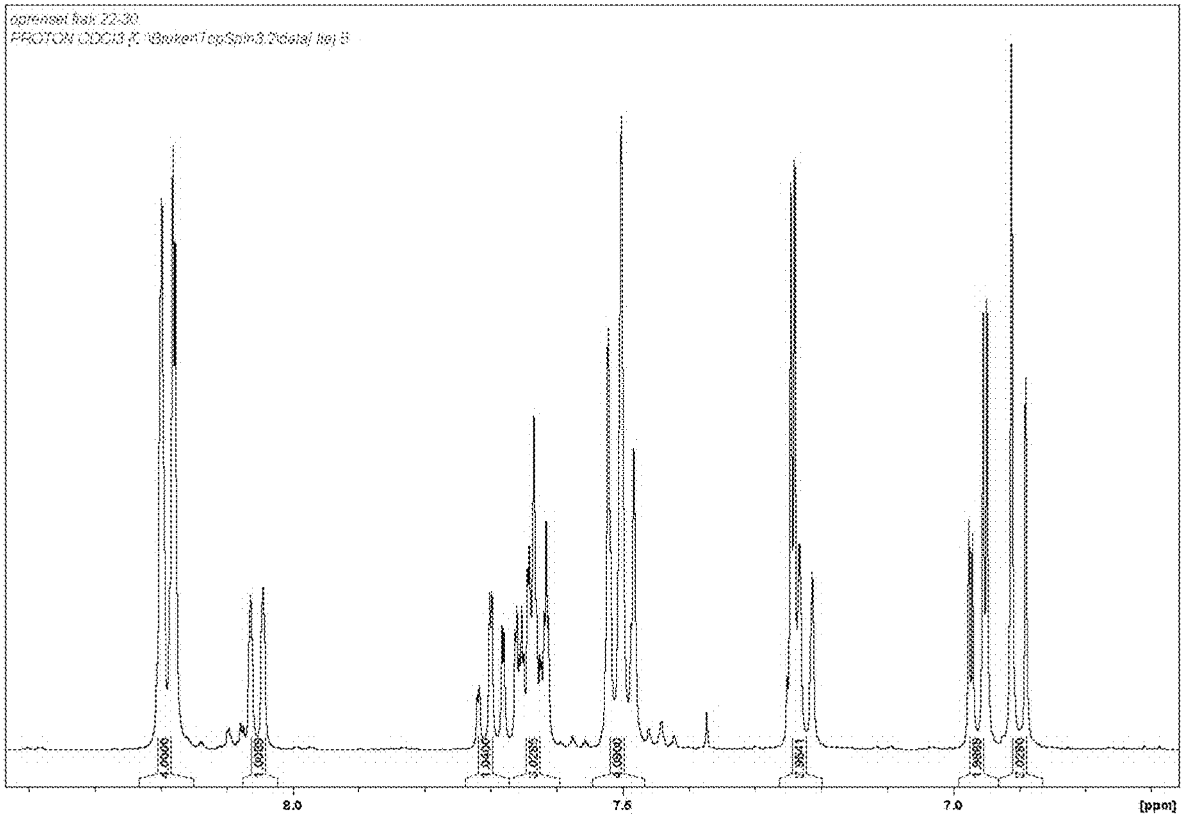
FIG. 1 is 1H NMR spectrum (400 MHz, $CDCl_3$) of Fluorescein dibenzoate

The present invention relates to a nanoparticle containing an indicators constituent(s), such nanoparticles can generate an indicative effect when the polymer of nanoparticle is degraded or broken, and therefore can be used for screening polymer degrading enzymes or degrading microorganism.

A nanoparticle of the present invention comprises water-insoluble polymer matrix and an indicator constituent(s), wherein the indicator constituent(s) is released from the nanoparticle only when the polymer matrix is degraded or broken, preferably, wherein the indicator constituent is encapsulated in the water-insoluble polymer matrix.

In a preferred embodiment, the mass concentration of the water-insoluble polymer matrix is about 50-99.99%, preferably, about 80-99.99%, such as, about 90-99.99%, more preferably, about 95-99.99%, and the mass concentration of the indicator constituent is about 0.01-50%, preferably, about 0.01-20%, such as about 0.01-10%, more preferably, about 0.01-5%.

In a preferred embodiment, when the water-insoluble polymer matrix is degraded or broken, from which the indicator constituent can be released, and then an indicative effect is triggered or enhanced.

The present invention also relates nanoparticle comprising water-insoluble polymer matrix and an indicator constituent(s), wherein the mass concentration of the water-insoluble polymer matrix is 50-99.99%, preferably, 80-99.99%, and the mass concentration of the indicator constituent is 0.01-50%, preferably, 0.01-20%, the indicator constituent(s) is released from the nanoparticle only when the polymer matrix is degraded or broken, and then an indicative effect can be triggered or enhanced.

In a preferred embodiment, wherein the indicator constituent is encapsulated in the water-insoluble polymer matrix or coated by the water-insoluble polymer matrix.

In a preferred embodiment, when the water-insoluble polymer matrix is degraded or broken, from which the indicator constituent is released, and then an indicative effect is detected in the presence of a substance which triggers or enhances the indicative effect.

In a preferred embodiment, wherein the water-insoluble polymer matrix comprises or consists of an enzyme substrate, preferably, the water-insoluble polymer is selected from polyester, starch, saccharides, lipids, lignin, protein, nucleic acid, amylose, cellulose, pectin, chitin, fatty acids, lignin, alginate acid, hyaluronic acid, agar, mannan, xanthan gum, arabic gum, protein, DNA or RNA, preferably, the polyester is, for example, polybutylene terephthalate (PBT), polypropylene terephthalate (PTT), polyethylene terephthalate (PEN), polyethylene terephthalate, tetramethylene terephthalate (PTMT), polyethylene-4-oxybenzoate, polyethylene glycol, polyvinyl chloride, polyglycolic acid, polylactic acid, polyanhydride, polycaprolactone, polyacrylonitrile, polypropylene, polyvinyl alcohol.

In general, a "nanoparticle" refers to any particle having a diameter of less than 1000 nm, e.g., about 20 nm to about 500 nm, or about 30 nm to about 300 nm, or about 50 nm to about 150 nm. Disclosed nanoparticles may include nanoparticles having a diameter ranging from about 60 to about 200 nm, or from about 70 to about 150 nm, or from about 80 to about 130 nm.

In a preferred embodiment, the nanoparticles of the present invention have a core-shell structure, wherein the said indicator constituent(s) is a core, and the said water-insoluble polymer forms a shell, preferably, the indicator constituent(s) as the core is encapsulated in the said shell, such core-shell structure can be obtained by different nanoparticles preparation methods or by coating the water-insoluble polymer to the said indicator constituent(s). "Indicator constituent is encapsulated in water-insoluble polymer matrix" contains the situations that the indicator constituent is coated by the water-insoluble polymer.

A wide variety of methods for forming particles therefrom are known in the art, e.g., a nanoprecipitation process or a nanoemulsion process, such as single emulsion or double emulsion techniques, wherein the said polymer is dissolved in an organic solvent to form an organic phase. The spray-drying method can also be used to prepare the nanoparticles of the present invention. the organic solvent can be dichloromethane, chloroform, ethyl acetate, dioxane, ethyl ether, acetone, tetrahydrofuran, glacial acetic acid, and a mixture solvent of them, but is not limited to these.

In a preferred embodiment, the nanoparticles are formed by providing a solution comprising one or more polymers, and then contacting the solution with a polymer nonsolvent to produce the particle. The solution may be miscible or immiscible with the polymer nonsolvent. For example, a water-miscible liquid such as acetonitrile may contain the polymers, and particles are formed as the acetonitrile is contacted with water, a polymer nonsolvent, e.g., by pouring the acetonitrile into the water at a controlled rate. The polymer contained within the solution, upon contact with the polymer nonsolvent, may then precipitate to form particles such as nanoparticles. Two liquids are said to be "immiscible" or not miscible, with each other when one is not soluble in the other to a level of at least 10 percent by weight at ambient temperature and pressure. Typically, an organic solution (e.g., dichloromethane, acetonitrile, chloroform, tetrahydrofuran, acetone, formamide, dimethylformamide, pyridines, dioxane, dimethylsulfoxide, etc.) and an aqueous liquid (e.g., water, or water containing dissolved salts or other species, cell or biological media, ethanol, etc.) are immiscible with respect to each other. For example, the first solution may be poured into the second solution (at a suitable rate or speed). In some cases, particles such as nanoparticles may be formed as the first solution contacts the immiscible second liquid, e.g., precipitation of the polymer upon contact causes the polymer to form nanoparticles while the first solution is poured into the second liquid, and in some cases, for example, when the rate of introduction is carefully controlled and kept at a relatively slow rate, nanoparticles may form.

In a preferred embodiment, the nanoparticles can be formed by anti-solvent precipitation method. For example, one or more polymers together with fluorescent substrate are dissolved in an organic solvent, e.g. dichloromethane, acetonitrile, chloroform, tetrahydrofuran, acetone, formamide, dimethylformamide, pyridines, dioxane, dimethyl sulfoxide, etc, and then the solution is mixed with an anti-solvent of polymer(s), e.g. water. Solubility of polymer(s) in the solvent-antisolvent mixture is lowered compared to that in the original solvent, and in this way the precipitation of polymers happens because of supersaturation. Nanoparticles under controlled size could be generated when mixing process is well manipulated.

The term "polymer," as used herein, is given its ordinary meaning as used in the art, i.e., a molecular structure comprising one or more repeat units (monomers), connected by covalent bonds. The repeat units may all be identical, or in some cases, there may be more than one type of repeat unit present within the polymer. In some cases, the polymer can be biologically derived, i.e., a biopolymer. Non-limiting examples include peptides or proteins.

Any suitable polymer can be used in the nanoparticles of the present invention. Polymers can be natural or unnatural (synthetic) polymers.

In general, the polymer of the present invention is water-insoluble polymer. In a preferred embodiment, the polymer is selected from polyester, starch, saccharides, lipids, lignin, protein, nucleic acid, amylose, cellulose, pectin, chitin, fat acids, lignin, alginate acid, hyaluronic acid, agar, mannan, xanthan gum, arabic gum, protein, DNA, RNA, the polyester is, for example, polybutylene terephthalate (PBT), polypropylene terephthalate (PTT), polyethylene terephthalate (PEN), polyethylene terephthalate (PET), tetramethylene terephthalate (PTMT), polyethylene-4-oxybenzoate, polyethylene glycol, polyvinyl chloride, polyglycolic acid, polylactic acid, polyanhydride, polycaprolactone, polyacrylonitrile, polypropylene, polyvinyl alcohol.

In a preferred embodiment, "polyester" as used herein means a linear polymeric molecule containing in-chain ester groups and which are derived from the condensation of a diacid with a diol or from the polymerization of hydroxy acids. The present invention applies to both aliphatic and aromatic polyesters. However, particularly preferred are aromatic polyester articles which are used to produce fiber and resin and that comprise a synthetically produced long chain polymer comprising at least 85%, preferably at least 90% and most preferably at least 95%, by weight of an ester of a substituted aromatic carboxylic acid, such as substituted terephthalic acid or parasubstituted hydroxybenzoate. Other useful polyester articles include those made of bulk polymer, yarns, fabrics, films, resins and powders. The principal polyesters in industrial usage include polyethylene terephthalate (PET), tetramethylene terephthalate (PTMT), polybutylene terphthalate (PBT), polytrimethylene terephthalate (PTT) and polyethylenenaphthalate (PEN), polycyclohexanedimethylene terephthalate (CHDMT), poly (ethylene-4-oxybenzoate) A-Tell, polyglycolide, and PHBA.

The polyester textile used herein is meant to include fibers, yarns, fabrics and garments comprising polyester. The polyester yarn or fabric or garment may be any yarn or fabric or garment that is made from pure poly (ethylene terephthalate), or that is made from blends of poly (ethylene terephthalate) fibers and any other material conventionally used for making textile.

In a preferred embodiment, the polyester fabric is a fabric blend comprising more than 35% (w/w) of polyester, in particular more than 50%, more than 65%, more than 90%, or more than 95% of polyester. In a most preferred embodiment, the process of the invention is applied to fabrics or garments consisting essentially of poly (ethylene terephthalate) polyester material, i.e. pure poly (ethylene terephthalate) polyester material.

In a preferred embodiment, wherein the indicator constituent is a fluorogenic indicator or chromonic indicator, for example, a fluorogenic or chromonic indicator conjugate having enzyme substrate, preferably, a fluorogenic or chromonic enzyme substrate, wherein the activity of a specific enzyme converts the fluorogenic or chromonic enzyme substrate into an indicative compound, for example, fluorescein.

In a preferred embodiment, wherein the indicator constituent is a fluorogenic indicator or chromonic indicator, for example, a fluorogenic or chromonic indicator conjugate having enzyme substrate, or a fluorogenic or chromonic enzyme substrate. The indicator constituent of the present invention is such as, benzoyl ester, fluorescein dibenzoate, Nile red, Nile blue A, 4-Methylumbelliferyl 2-Sulfamino-2-deoxy-alpha-D-glucopyranoside, 4-Methylumbelliferyl butyrate, 4-Methylumbelliferyl Oleate, 4-Methylumbelliferyl sulfate, D-Luciferin, Resorufin, N-Butylfluorescein, Dansylcadaverine, Glutaryl-L-phenylalanine 7-amido-4-methylcoumarin, O-Methyl-O—(N-Butylfluorescein)phosphate, 3-Acetylumbelliferyl beta-D-glucopyranoside, 4-Methylumbelliferyl alpha-L-iduronide, Fluorescein dicaprylate WS1, Hoechst 34580, Dihydrotetramethylrosamine.

In a preferred embodiment, a desired optical signal from indicator constituent such as a fluorescent indicator compound indicates that the bioactive substance of interest, for example, enzyme or microorganism is capable of degrading or assisting in degrading water-insoluble polymers.

Non-limiting examples of suitable indicator constituents in accordance with the present disclosure include stilbene derivatives, styryl derivatives of benzene and biphenyl, pyrazolines, bis(benzoxazol-2-yl) derivatives, coumarins, carbostyrils, or mixtures thereof.

In some embodiments, fluorescent dyes suitable for use as indicator constituents in accordance with the present disclosure include naphthalimide dyes, coumarin dyes, xanthenes dyes, thioxanthene dyes, naphtholactam dyes, azlactone dyes, methane dyes, oxazine and thiazine dyes, and combinations thereof. The dyes are added in an amount sufficient to highlight residual cellulose after a hydrolysis reaction. The dyes should not be added in amounts that create excessive background highlighting of other constituents of the reaction medium.

In some embodiments, the indicator constituents of the present disclosure are suitable for creating a signal. The signal may be electromagnetic radiation such as light rays on the electromagnetic spectrum. For example, the signal may be characterized as having a wavelength in the UV, Vis, or NIR portion of the electromagnetic spectrum. In embodiments, the signal is characterized as luminescent, or any process in which energy is emitted from a material at a different wavelength from that at which it is absorbed. In embodiments, the signal is characterized as fluorescent or having fluorescence. Fluorescent signal incorporates a phenomenon in which electron de-excitation occurs almost spontaneously, and in which emission from a luminescent substance ceases when an exciting source is removed. Thus, it is envisioned that embodiments herein include a step of exciting the indicator constituent. For example, electromagnetic radiation may be applied to the indicator constituent so that it may emit energy or a signal such as at a predetermined intensity.

In some embodiments, the signal is such that it can be detected by a microplate reader. A microplate reader is a laboratory instrument designed to detect biological, chemical, or physical events of samples in one or more microtiter plates. Sample reactions can be assayed in, inter alia, 6-1536 well format microtiter plates. Typically, a high-intensity lamp passes light to the microtiter well and the light emitted by the reaction happening in the microplate well is quantified by a detector. Common detection modes for microplate assays are absorbance, fluorescence intensity, luminescence, time-resolved fluorescence, and fluorescence polarization.

In a preferred embodiment, wherein both the polymer matrix and indicator constituent have similar or same enzymatic hydrolysis group, preferably, both the polymer matrix and indicator constituent can be both degraded or hydrolyzed by a specific active enzyme, and then, an indicative effect, such as a fluorescence indicative effect, is triggered or enhanced.

In a preferred embodiment, wherein the polymer matrix can be degraded or hydrolyzed by a specific active enzyme, thereby releasing the indicator constituent, and such indicator constituent can further be degraded or hydrolyzed by a second specific active enzyme, and then, an indicative effect, such as a fluorescence indicative effect, is triggered or enhanced, alternatively, an indicative effect, such as a fluorescence indicative effect, is triggered or enhanced when such indicator constituent is dissolved in solution. In a preferred embodiment, for example, the fluorescein, when it is solid or condensed, it is non-fluorescence or low-fluorescence due to self-quenching, but it can convert to a substance with high fluorescence when it is dissolved in a liquid solution.

The present invention also relates to a method for screening a bioactive substance of a library which is capable of degrading or assisting in degrading water-insoluble polymers, comprising the steps of:

a) provide nanoparticles of the present invention;

b) contact the bioactive substance to be analyzed with the nanoparticles of the present invention to form a mixture;

c) when the indicative effect produced by the indicator is triggered or enhanced, it indicates that the biologically active substance can degrade or assist in degrading the water-insoluble polymer matrix constituting the nanoparticles.

In a preferred embodiment, when the indicative effect reaches or is above a preset threshold level, it indicates that the biologically active substance can degrade or assist in degrading the water-insoluble polymer matrix constituting the nanoparticles.

In a preferred embodiment, wherein the bioactive substance of interest is a water-insoluble polymer degrading enzyme or a water-insoluble polymer degrading microorganism, such as a water-insoluble polymer degrading bacterium, such as bacteria, fungi, actinomycetes or archaea, preferably, the water-insoluble polymer degrading microorganism is capable of expressing a water-insoluble polymer degrading enzyme or capable of expressing an enhancer of a water-insoluble polymer degrading enzyme.

In a preferred embodiment, wherein the library is an enzyme library or a or microorganism library, comprising a multitude of different enzymes or microorganism, wherein the amount of indicative effect released by one enzyme or a microorganism reaches or is above the predetermined threshold level, whereby a targeted enzyme or a targeted microorganism is identified.

In a preferred embodiment, wherein the library is an enzyme library comprising a multitude of enzyme variants derived from a parent enzyme, wherein an increased amount of indicative effect has been released by the active enzyme variant, as compared with the parent enzyme, whereby an improved enzyme variant is identified.

In a preferred embodiment, the enzyme is a polymer matrix degrading enzyme, such as a hydrolase, isomerase, ligase, lyase, oxidoreductase, or transferase, preferably, the enzyme of interest is an alpha-galactosidase, alpha-glucosidase, aminopeptidase, amylase, asparaginase, beta-galactosidase, beta-glucosidase, beta-xylosidase, sugar enzyme, carboxypeptidase, catalase, cellobiohydrolase, cellulase, chitin enzyme, cutinase, lipolytic enzyme, peroxidase, cyclase, cyclodextrin glycosyltransferase, deoxyribonuclease, endoglucanase, esterase, green fluorescent protein, dextran transferase, glucoamylase, invertase, laccase, lipase, mannosidase, mutase, oxidase, pectin lyase, peroxidase, phytase, polyphenol oxidase, proteolytic enzyme, ribonuclease, transglutaminase, xylanase, PET degrading enzyme or horseradish peroxidase.

Cutinases are lipolytic enzymes classified as EC 3.1.1.74 according to Enzyme Nomenclature. Reference is made to the Recommendations of the Nomenclature Committee of the International Union of Biochemistry and Molecular Biology, Academic Press Inc., 1992.

For purposes of the present invention, cutinase activity is determined using oligomer Terephtalic acid-bis-2-benzoyloxy-ethylesther (BETEB) as substrate according to Example 1 of the present invention. BETEB is a by-product during the PET synthesis and is generally remained in the fabric or garment during textile manufacturing. BETEB is produced by e.g. condensation of terephthalic acid, benzoic acid and ethylene glycol, which has the same unit of benzoyloxy-ethylester as PET.

Cutinases are known from various fungi, such as a filamentous fungal cutinase, e.g. native to a strain of *Humicola* or *Fusarium*, specifically *H. insolens* or *F. solani pisi*, more specifically *H. insolens* strain DSM 1800 (U.S. Pat. No. 5,827,719), or particularly *F. solani pisi* (WO 90/09446; WO 94/14964, WO 94/03578).

The fungal cutinase may also be derived from a strain of *Rhizoctonia*, e.g. *R. solani*, or a strain of *Alternaria*, e.g. A. *Brassicicola* (WO 94/03578). The cutinase enzyme may also be a variant of a parent cutinase such as those described in WO 00/34450, or WO 01/92502.

In a preferred embodiment, polymer degrading microorganism may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma.*

In a preferred embodiment, polymer degrading microorganism may be any fungus cells including, but not limited to *Aspergillus fumigatus, Aspergillus oryzae, Aspergillus sojae, Candida colliculosa, Candida_tropicalis, Debaryomyces hansenii, Geotrichum candidum, kazachstania exigua, Kluyveromyces lactis, Kluyveromyces marxianus, Penicillium nalgiovense, Rhodotorula glutinis, Saccharomyces bayanus, Saccharomyces carlsbergensis, Saccharomyces cerevisiae, Torulaspora delbrueckii*, and *Yarrowia lipolytica.*

In a preferred embodiment, polymer degrading microorganism may be any archaea cells including, but not limited to *Metallosphera sedula, Methanobacterium thermoautotrophicum, Methanococcus jannaschii, Pyrococcus abyssi, Pyrococcus furiosus, Sulfolobus shibatae, Sulfolobus solfataricus, Thermococcus barosii*, and *Thermococcus litoralis.*

In a preferred embodiment, polymer degrading microorganism may be any actinomycetes cell including, but not limited to *Nocardia nova, Actinopolyspora halophila, Microbisporarosea* subsp. *aerata, Planotetraspora mira, Herbidospora cretacea, Planomonospora parontospora, Stretoalloteichus hindustanus.*

In a preferred embodiment, the said polymer degrading microorganism may be any plant cell.

In a preferred embodiment, polymer degrading microorganism cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis.*

In a preferred embodiment, polymer degrading microorganism may also be any *Streptococcus* cell including, but not limited to, *Streptococcus equisimilis, Streptococcus pyogenes, Streptococcus uberis*, and *Streptococcus equi* subsp. *Zooepidemicus* cells.

In a preferred embodiment, polymer degrading microorganism may also be any *Streptomyces* cell including, but not limited to, *Streptomyces achromogenes, Streptomyces avermitilis, Streptomyces coelicolor, Streptomyces griseus*, and *Streptomyces lividans* cells.

In a preferred embodiment, the said library of the present invention encodes enzyme of interest, for example, one or more enzyme selected from the following group: hydrolase, isomerase, ligase, lyase, oxidoreductase, or transferase; preferably the library encodes one or more alpha-galactosidase, alpha-glucosidase, aminopeptidase, amylase, asparaginase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, green fluorescent protein, glucano-transferase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

In a preferred embodiment, the said bioactive substance of interest of the present invention is polynucleotide encoding an enzyme or a cell expressing an enzyme.

In a preferred embodiment, the said library of the present invention is a library of polynucleotides expression systems, preferably, the said library is a library of natural cells or recombinant cells, preferably, natural cells or recombinant cells of bacteria, fungi, archaea, actinomycete and/or plant.

In one preferred embodiment, the said library of the present invention encodes different variants of the same enzyme and in another, the said library comprises two or more different polynucleotides encoding the same enzyme.

It is envisioned that the method of the present invention may employ a library of isolated polynucleotides and/or in vitro expression systems. However, a preferred embodiment of the invention is an in vivo setup, wherein the library is comprised within a prokaryotic host cell; preferably within a Gram-positive host cell; more preferably within a *Bacillus* host cell; even more preferably within a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, or *Bacillus thuringiensis* host cell; and most preferably within a *Bacillus licheniformis* host cell. Naturally, each individual polynucleotide of the library is in its own separate host cell.

The techniques used to isolate or clone a polynucleotide are known in the art and include isolation from genomic DNA or cDNA, or a combination thereof. The cloning of the polynucleotides from genomic DNA can be effected, e.g., by using the well known polymerase chain reaction (PCR) or antibody screening of expression libraries to detect cloned DNA fragments with shared structural features. See, e.g., Innis et al., 1990, PCR: A Guide to Methods and Application, Academic Press, New York. Other nucleic acid amplification procedures such as ligase chain reaction (LCR), ligation activated transcription (LAT) and polynucleotide-based amplification (NASBA) may be used.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variants may be constructed on the basis of the polynucleotide presented as the mature polypeptide coding sequence, e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, Protein Expression and Purification 2: 95-107.

The present invention also relates to screen recombinant cells, preferably, recombinant host cells which comprise a polynucleotide operably linked to one or more control sequences that direct the production of a polypeptide of the present invention. A construct or vector comprising a polynucleotide is introduced into a recombinant cell so that the construct or vector is maintained as a chromosomal integrant or as a self-replicating extra-chromosomal vector as described earlier. The term "recombinant cell" encompasses any progeny of a parent cell that is not identical to the parent cell due to mutations that occur during replication. The choice of a host cell will to a large extent depend upon the gene encoding the polypeptide and its source.

The recombinant cell may be any cell useful in the recombinant production of a polypeptide of the present invention, e.g., a prokaryote.

The prokaryotic recombinant cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial recombinant cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial recombinant cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial recombinant cell may also be any *Streptomyces* cell including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, Mol. Gen. Genet. 168: 111-115), competent cell transformation (see, e.g., Young and Spizizen, 1961, J. Bacteriol. 81: 823-829, or Dubnau and Davidoff-Abelson, 1971, J. Mol. Biol. 56: 209-221), electroporation (see, e.g., Shigekawa and Dower, 1988, Biotechniques 6: 742-751), or conjugation (see, e.g., Koehler and Thorne, 1987, J. Bacteriol. 169: 5271-5278). The introduction of DNA into an *E. coli* cell may be effected by protoplast transformation (see, e.g., Hanahan, 1983, J. Mol. Biol. 166: 557-580) or electroporation (see, e.g., Dower et al., 1988, Nucleic Acids Res. 16: 6127-6145). The introduction of DNA into a *Streptomyces* cell may be effected by protoplast transformation, electroporation (see, e.g., Gong et al., 2004, Folia Microbiol. (Praha) 49: 399-405), conjugation (see, e.g., Mazodier et al., 1989, J. Bacteriol. 171: 3583-3585), or transduction (see, e.g., Burke et al., 2001, Proc. Natl. Acad. Sci. USA 98: 6289-6294). The introduction of DNA into a *Pseudomonas* cell may be effected by electroporation (see, e.g., Choi et al., 2006, J. Microbiol. Methods 64: 391-397) or conjugation (see, e.g., Pinedo and Smets, 2005, Appl. Environ. Microbiol. 71: 51-57). The introduction of DNA into a *Streptococcus* cell may be effected by natural competence (see, e.g., Perry and Kuramitsu, 1981, Infect. Immun. 32: 1295-1297), protoplast transformation (see, e.g., Catt and Jollick, 1991, Microbios 68: 189-207), electroporation (see, e.g., Buckley et al., 1999, Appl. Environ. Microbiol. 65: 3800-3804), or conjugation (see, e.g., Clewell, 1981, Microbiol. Rev. 45: 409-436). However, any method known in the art for introducing DNA into a host cell can be used.

In a preferred embodiment of the present invention, wherein the indicative effect is a fluorescent indicative effect.

In a preferred embodiment, the indicative effect is an indicative signal, preferably, a fluorescent signal.

A test card, microwell array, capillary array, microfluidic device, sensor disk array, a kit or other apparatus is provided having a plurality of wells, compartments, or isolated supports which separately contain the nanoparticles of the present invention can be used in screening bioactive substances capable of degrading or assisting in degrading water-insoluble polymers.

The present invention also relates to a microfluidic or "lab-on-a-chip" method. More specifically, it relates to how to use fluid-injection as a means for selecting or deselecting droplets of water in an immiscible carrier fluid. The water droplets are sometimes referred to as microdroplets or microencapsulations, they typically have an average diameter of about 20 micrometers and are used as compartments or minuscule reaction vessels. They can contain live microbial cells that are, for example, secreting an enzyme. The droplets may also contain other components, for example, a fluorogenic enzyme substrate that can reveal the activity of an enzyme produced by a microbial cell within a droplet.

The present invention also relates to a microreactor comprising the nanoparticles of the present invention and at least one biologically active substance, the microreactor can be in the form of an aqueous phase, for example in the form of a water droplet, which can be dispersed in the oil phase, or in the form of an oil water droplet, which can be dispersed in the water phase.

In a preferred embodiment, the said microreactor has an average diameter of about 1 to 200 microns, preferably 2 to 100 microns, more preferably 10 to 50 microns, more preferably 10 to 30 microns, for example 15 to 25 microns.

In a preferred embodiment, the said microreactor is a microdroplet. The microdroplet library may be heterogeneous with respect to cellular content, and some microdroplets may be empty. Fluorescence-Activated Droplet Sorting (FADS), it can be used in high-throughput, massively parallel screens so that very large numbers of different producer cell mutants can be screened against a wide range of different target cells. FADS may be used to manipulate the microdroplets at any stage after their formation in the methods of the invention, but are preferably used at least to screen the library of microcultures those in which target cells have been outgrown or overgrown to extinction by mutant producer cells. FADS may also be used during the co-encapsulation step, for example to eliminate empty microdroplets which do not contain mutant producer and/or target cell(s). Either or both mutant producer cells and target cells may be fluorescently labelled to enable FADS. A variety of fluorescent proteins can be used as labels for this purpose, including for example the wild type green fluorescent protein (GFP) of *Aequorea victoria* (Chalfie et al. 1994, Science 263:802-805), and modified GFPs (Heim et al. 1995, Nature 373:663-4; PCT publication WO 96/23810). Alternatively, DNA2.0's IP-Free(C) synthetic non-*Aequorea* fluorescent proteins can be used as a source of different fluorescent protein coding sequences that can be amplified by PCR or easily excised using the flanking Bsal restriction sites and cloned into any other expression vector of choice.

The present invention also relates to an enzyme screening or selection method, comprising the steps of:

a) providing an enzyme library and a multitude of compartments, each compartment comprising an aliquot of liquid and at least one solid composition comprising a mixture of an enzyme substrate (preferably 50-99.99% (w/w)) and a sufficient amount of enzyme substrate conjugated to a fluorophore or chromophore marker (preferably 50-0.01% (w/w));
b) contacting the solid composition in each compartment with an enzyme of the library, wherein both the substrate and substrate-marker conjugate are degraded by an active enzyme, thereby releasing the fluorophore or chromophore marker;
c) identifying one or more compartment, wherein the fluorophore or chromophore marker has been released by the active enzyme, thereby identifying the active enzyme.

In a preferred embodiment, wherein the enzyme library comprises a multitude of enzyme variants derived from a parent enzyme, and wherein a compartment is identified in step (c), wherein an increased amount of marker has been released by the active enzyme variant, as compared with the parent enzyme, whereby an improved enzyme variant is identified.

In a preferred embodiment, wherein the said solid composition comprises or consists of the nanoparticles of the present invention.

In a preferred embodiment, wherein the said compartment comprises or consists of the microreactor of the present invention.

In a preferred embodiment, wherein the said enzyme substrate comprises or consists of the water-insoluble polymers of the present invention.

In a preferred embodiment, wherein the said enzyme substrate conjugated to a fluorophore or chromophore marker is a fluorogenic indicator or chromonic indicator, for example, a fluorogenic or chromonic indicator conjugate having enzyme substrate, preferably, a fluorogenic or chromonic enzyme substrate, wherein the activity of a specific enzyme converts the fluorogenic or chromonic enzyme substrate into an indicative compound, for example, fluorescein.

In a preferred embodiment, wherein the mass concentration of the said enzyme substrate of the said solid composition is 50-99.99%, preferably, 80-99.99%, or 90-99.99%, such as, 95-99.9%, and the mass concentration of the said enzyme substrate conjugated to a fluorophore or chromophore marker of the said solid composition is 0.01-59%, preferably, 0.01-20%, or 0.01-10%, such as 0.1-5%.

The present invention also relates to a method for screening a bioactive substance of a library which is capable of degrading or assisting in degrading the water-insoluble polymer matrix using a microfluidic-based system, comprising:

a) droplet generation process, wherein droplet containing biologically active substances are generated;
b) nanoparticles introducing process, wherein a secondary droplet containing the nanoparticles of the present invention is coalesced with the droplet generated by unit (a);
c) droplets sorting process, wherein the targeted droplets are sorted based on the indicative effect generated by the indicator, and
d) analysis and detection process, wherein the sorted targeted droplets are further analyzed to screen the targeted biologically active substance.

The present invention also relates to a method for screening a bioactive substance of a library which is capable of degrading or assisting in degrading the water-insoluble polymer matrix using a microfluidic-based system, comprising:

a) droplet generation process, wherein an aqueous liquid droplet is generated;
b) nanoparticles introducing process, wherein a droplet containing the nanoparticles of of the present invention is coalesced with the droplet generated by unit (a);
c) bioactive substance introducing process, wherein a droplet containing the bioactive substance of a library is coalesced with the droplet generated by unit (a);
d) droplets sorting process, wherein the targeted droplets are sorted based on the indicative effect generated by the indicator, and
e) analysis and detection process, wherein the sorted targeted droplets are further analyzed to screen the targeted biologically active substance, wherein process b) can be performed simultaneously, before or after and process c), or process a), process b) and process c) can be performed simultaneously.

The present invention also relates to a microfluidic-based screening system for a bioactive substance of a library, comprising:

a) droplets generation unit, wherein droplets containing biologically active substances are generated;
b) nanoparticles introducing unit, wherein a secondary droplet containing the nanoparticles of the present invention is coalesced with the droplet generated by unit (a), or wherein the nanoparticles of the present invention are mixed with the droplet generated by unit (a);
c) droplets sorting unit, wherein the targeted droplets are sorted based on the indicative effect generated by the indicator, and
d) analysis and detection unit, wherein the sorted targeted droplets are further analyzed to screen the biologically active substance of a library which have the biologically activity to degrade or assist in degrading the water-insoluble polymer matrix.

In a preferred embodiment, when the indicative effect of the droplet reaches or is above a preset threshold level, the droplet sorting system triggers the selection of the target droplet, preferably, the droplet sorting system triggers the deflection of the target droplet toward selection paths, for further droplet analysis.

In a preferred embodiment, the droplet sorting is based on a fluorescence activated droplet sorting technique.

In a preferred embodiment, wherein the microfluidic-based screening method further comprises a droplet incubation process, wherein the droplets containing the biologically active substance are incubated.

In a preferred embodiment, wherein the microfluidic-based screening system further comprises a droplet incubation unit, wherein the droplets containing the biologically active substance are incubated.

In a preferred embodiment, wherein the microfluidic-based screening system further comprises an injection unit, wherein a substance, for example, that can trigger or enhance the indicative effect of the indicator constituent, such as a second enzyme, is injected into the droplet before sorting.

In a preferred embodiment, wherein the nanoparticles introduction unit is a nanoparticles picoinjection unit, wherein a picoliter volume of nanoparticles solution can be introduced into the droplet.

In a preferred embodiment, wherein the said nanoparticles introduction process is a nanoparticles picoinjection process, wherein a picoliter volume of nanoparticles solution can be introduced into the droplet, preferably, a picoliter volume of aqueous liquid solution comprising nanoparticles can be introduced into the droplet.

In a preferred embodiment, wherein the said bioactive substance introducing process is a picoinjection process, wherein a picoliter volume of aqueous liquid solution comprising bioactive substance can be introduced into the droplet.

In a preferred embodiment, the wherein the microfluidic-based screening method further comprises an injection unit, wherein a substance, for example, that can trigger or enhance the indicative effect of the indicator, such as a second enzyme, is injected into the droplet before sorting.

In a preferred embodiment, wherein each droplet before sorting comprises at most a single cell.

The activity of the one or more enzyme encoded by a polynucleotide library or expressed by a microorganism is assayed either qualitatively or quantitatively by detecting the conversion of an enzyme substrate into a detectable or quantifiable enzyme product. Typically, a fluorogenic enzyme substrate is added which is turned into a fluorescent enzyme product to be detected or measured.

In a preferred embodiment, wherein the library is a microorganism library comprising a multitude of different microorganism, wherein the amount of indicative effect released by microorganism reaches or is above the predetermined threshold level, whereby a targeted enzyme or a targeted microorganism is identified.

In a preferred embodiment, wherein the bioactive substance library, such as an enzyme library comprises a multitude of enzyme variants derived from a parent enzyme, wherein an increased amount of indicative effect has been released by the active enzyme variant, as compared with the parent enzyme, whereby an improved enzyme variant is identified.

In a preferred embodiment, once a particularly interesting enzyme activity has been detected in a selected droplet, the polynucleotide library member inside the droplet needs to be identified. Typically, the polynucleotide is identified through DNA sequencing.

Where used herein and unless specifically indicated otherwise, the following terms are intended to have the following meanings in addition to any broader (or narrower) meanings the terms might enjoy in the art.

Unless otherwise required by context, the use herein of the singular is to be read to include the plural and vice versa. The term "a" or "an" used in relation to an entity is to be read to refer to one or more of that entity. As such, the terms "a" (or "an"), "one or more," and "at least one" are used interchangeably herein. As used herein, the term "comprise," or variations thereof such as "comprises" or "comprising," are to be read to indicate the inclusion of any recited integer (e.g. a feature, element, characteristic, property, method/process step or limitation) or group of integers (e.g. features, element, characteristics, properties, method/process steps or limitations) but not the exclusion of any other integer or group of integers. Thus, as used herein the term "comprising" is inclusive or open-ended and does not exclude additional, unrecited integers or method/process steps.

The present invention is further described by the following examples that should not be construed as limiting the scope of the invention.

EXAMPLES

Example 1: Synthesis of Fluorescein Dibenzoate Indicator

Fluorescein dibutyrate (CAS 7298-65-9) is a commercialized fluorogenic substrate for esterase and lipase with ester bonds from aliphatic carboxylic acid. To better mimic the aromatic ester structure in PET (polyethylene terephthalate), fluorescein dibenzoate (formula I) was synthetized which could be degraded by PETase and produces fluorescein (λex=488 nm and λem=523 nm).

Fluorescein dibenzoate was synthesized as described by Poznik and König in Org. Biomol. Chem. 2014, 12, 3175-3180. Briefly, fluorescein (400 mg, 1.2 mmol, Sigma-Aldrich) was suspended in toluene (30 ml, Sigma-Aldrich) to which benzoyl chloride (423 uL, 3.6 mmol, Sigma-Aldrich), triethyl amine (503 uL, 3.6 mmol, Sigma-Aldrich) and DMAP (5 mg, Sigma-Aldrich) was added. The mixture was stirred 24 h under $N_2$ at room temperature. Thin-layer chromatography (TLC, EtOAc-heptane 3:1) showed full conversion of fluorescein. The mixture was purified by flash chromatography, eluting with a 0-100% gradient of EtOAc in heptane. The target compound was isolated in 605 mg (93% yield) and characterized by Nuclear Magnetic Resonance (NMR, Bruker) spectrums to confirm the structure.

Figure 2:
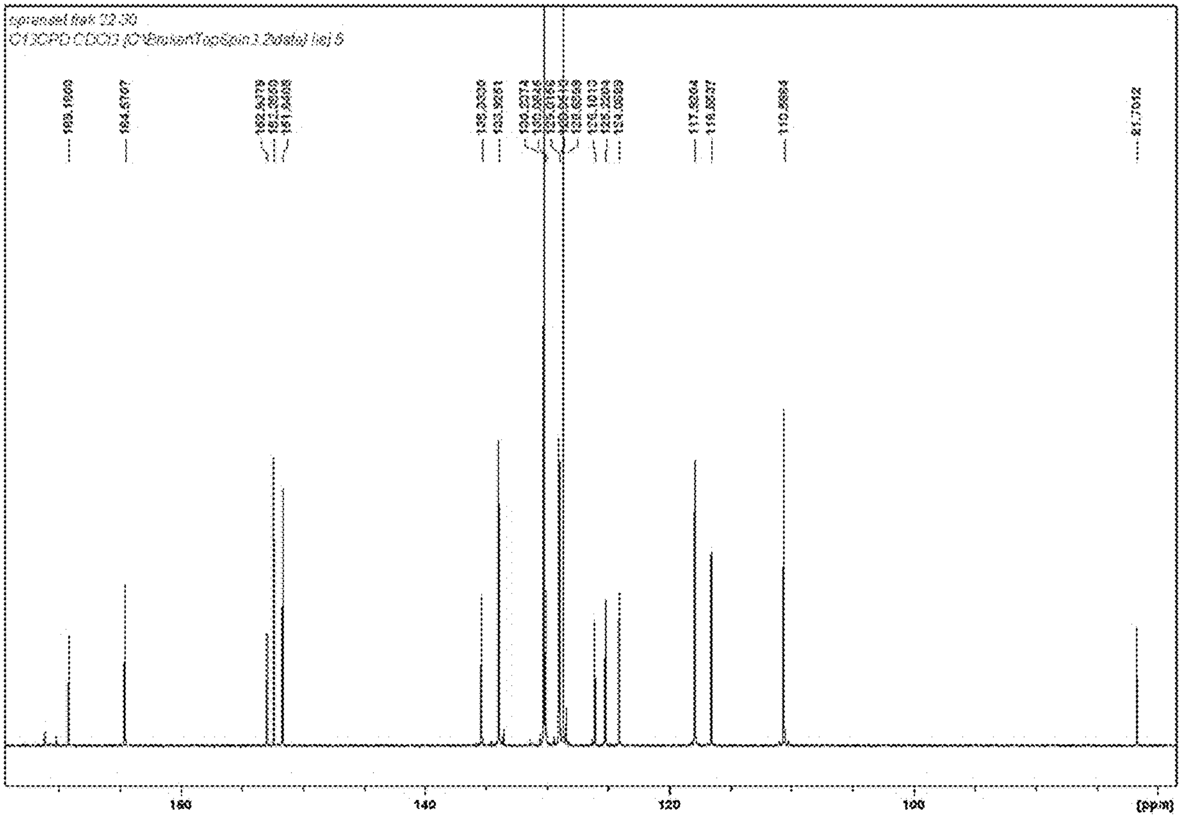
FIG. 2 is 13C NMR spectrum (100 MHz, $CDCl_3$) of Fluorescein dibenzoate

Fluorescein dibenzoate: 1H-NMR (FIG. 1, 400 MHz; CDCl3): δ 8.24-8.15 (m, 4H), 8.05 (d, 1H), 7.75-7.59 (m, 4H), 7.47-7.55 (t, 4H), 7.27-7.19 (m, 3H), 6.97-6.99 (dt, 4H). 13C-NMR (FIG. 2, 100 MHz; CDCl3): δ 169.21, 164.62, 152.99, 152.41, 151.70, 135.39, 134.59, 134.25, 133.98, 133.57, 130.63, 130.58, 130.29, 130.14, 130.03, 129.07, 129.01, 128.92, 128.71, 128.47, 126.32, 126.16, 125.28, 124.14, 117.98, 116.61, 110.64, 81.76.

(I)

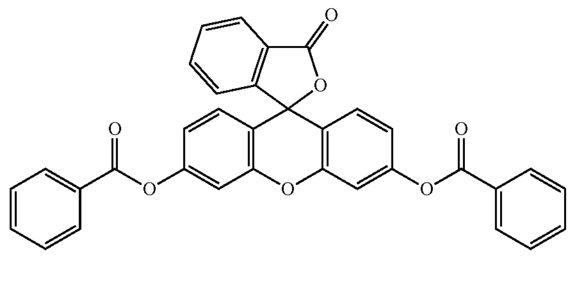

Example 2: Preparation of PET Nanoparticles

Firstly, 0.05 g PET fiber (provided by Sinopec Yizheng Chemical Fiber Co., Ltd.) was dissolved in 5 mL Hexafluoroisopropanol (HFIP, Shanghai Shaoyuan Co. Ltd., Shanghai, China); and after dissolving, 0.025 g Fluorescein dibenzoate (prepared in Example 1) was added into the solution. Remove the plug of a 15 mL glass syringe (15 ml, Runze Fluid, Nanjing, China), and fill the above solution into the syringe from back. Then install the plug back and remove bubble in the syringe and get Teflon tubing (i.d. 0.6 mm, o.d. 0.8 mm, from Zeus) connected with its needle. Add 10 mL DI water in a 25 mL beaker. Immerse the cutter head in the water and adjust the speed of the high-speed stirrer (Fluko, Shanghai, China) to 19,000 rpm. Add the solution into the beaker drop by drop, at flow rate of 0.1 mL/min using the syringe pump (Longerpump, Hebei, China).

Figure 3:
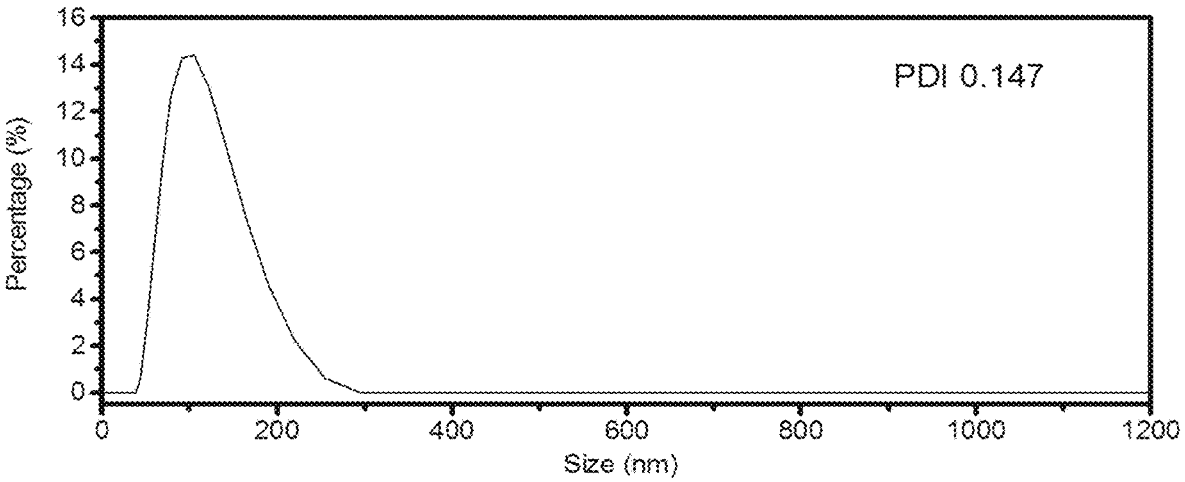
FIG. 3 shows the Dynamic Light Scattering (DLS) of prepared PET nanoparticles

After all solution were pumped into the beaker, the mixture of nanoparticle suspension was filtered through a filter paper (Whatman filter paper, Cat. No. 597, GE Healthcare, UK) into a round-bottom flask. Then the solvent (HFIP) in the solution was removed by rotary evaporation under vacuum at 30° C. in a rotary evaporator (RE-52AA, Yarong, Shanghai, China). After 20 minutes, the nanoparticle solution was filtered again using the same filter paper, and the final volume was adjusted to 10 mL using DI water. The obtained nanoparticles have an average diameter of 97.94 nm under Dynamic Light Scattering (DLS, Zetasizer Nano-ZS 90, Malvern Instruments) (Polydispersity index, PDI: 0.147) (FIG. 3). Then, 100 μL DMSO (from Amresco) was added to 1 mL nanoparticle solution in a 1.5 mL Eppendorf tube, and the tube was vortexed for 20 s to remove residual and free Fluorescein dibenzoate substrate in the surface of PET Nanoparticles. Then the mixture was centrifugated at 12,000 rpm, 4° C., 20 min on centrifugal machine (Centrifuge 5418 R, Eppendorf). Then the supernatant was removed, and 1 mL DI water was added, such washing procedures were repeated several times. The tube was then sonicated 5 s for resuspension of nanoparticles using an ultrasonicator (50 Hz, 80 W, Ultrasonic Cleaner DR-MS07, Derui). Then the nanoparticle suspension is ready for use now. The encapsulated Fluorescein dibenzoate was 34% (w/w) in nanoparticles, and this value was obtained by the determination of fluorescence intensity releasement of pre-unit mass Fluorescein dibenzoate and per-unit mass nanoparticles after the hydrolysis with overdosed enzymes. Specifically, 10 μg Fluorescein dibenzoate released the fluorescence intensity of 450 relative fluorescence unit (RFU). For prepared PET nanoparticles, 50 μg Nanoparticles released the fluorescence intensity of about 7600 RFU, and this value was equivalent to the fluorescence releasement from 17 μg Fluorescein dibenzoate.

Figure 4:
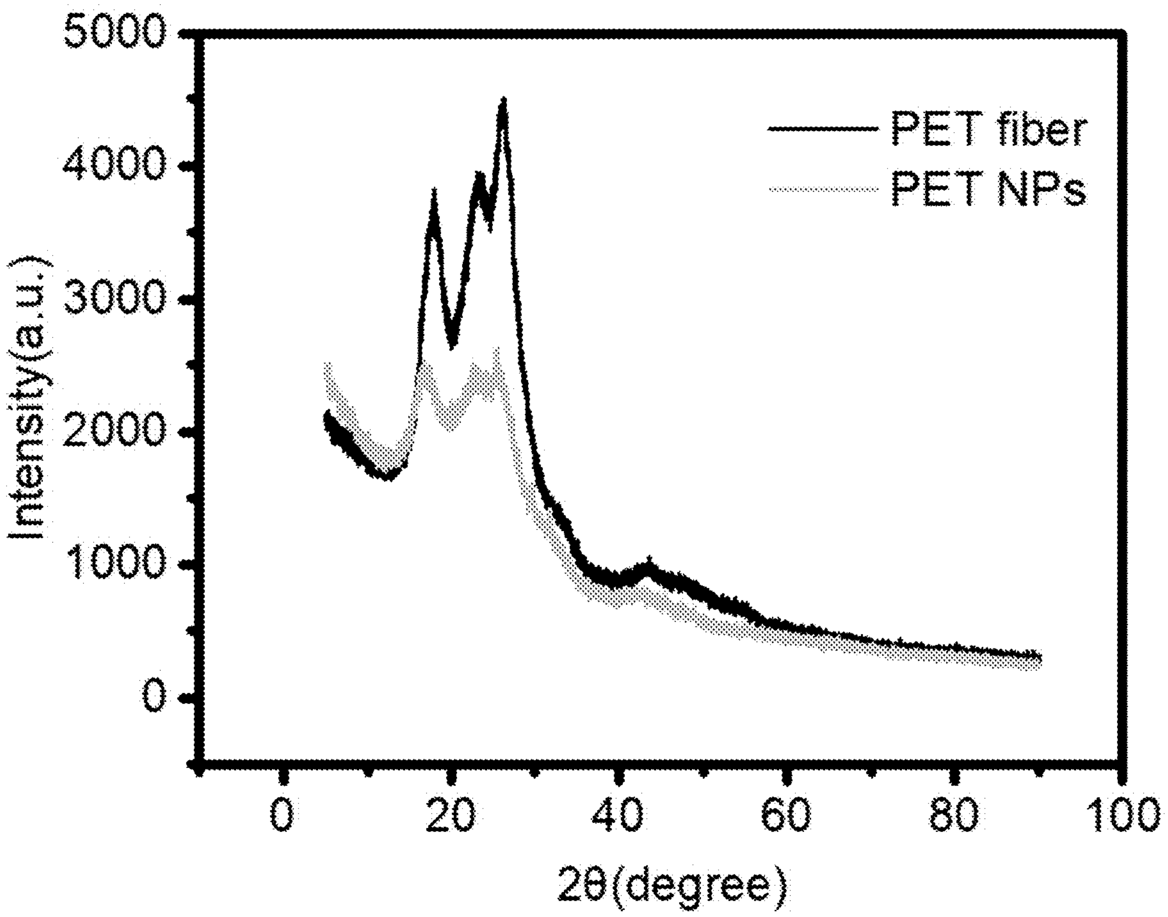
FIG. 4 shows the X-ray Diffraction (XDR) of PET fiber and prepared PET nanoparticles; NPs was short name of nanoparticles

PET fiber has crystal structure which is a key property for the degradation by bioactive substance because the crystal structure will influence the accessibility of the enzymatic targeting cleavage sites. Therefore, prepared PET nanoparticles were measured by X-ray Diffraction (XRD) on Rigaku SmartLab X-ray diffractometer (Rigaku, USA) within the 2θ angle range from 5° to 90° for crystal structure analysis. FIG. 4 shows XRD patterns for PET nanoparticles and PET fiber. Both materials exhibit three peaks at 2θ of about 18°, 23° and 26°, which indicates that PET fiber and nanoparticles have the same crystal form. The retaining crystal structure in nanoparticles is important to ensure a good correlation of prepared nanoparticles to original fiber in application.

Example 3: PET Nanoparticles for Enzyme Screening in 96-Well Microtiter Plate

Figure 5:
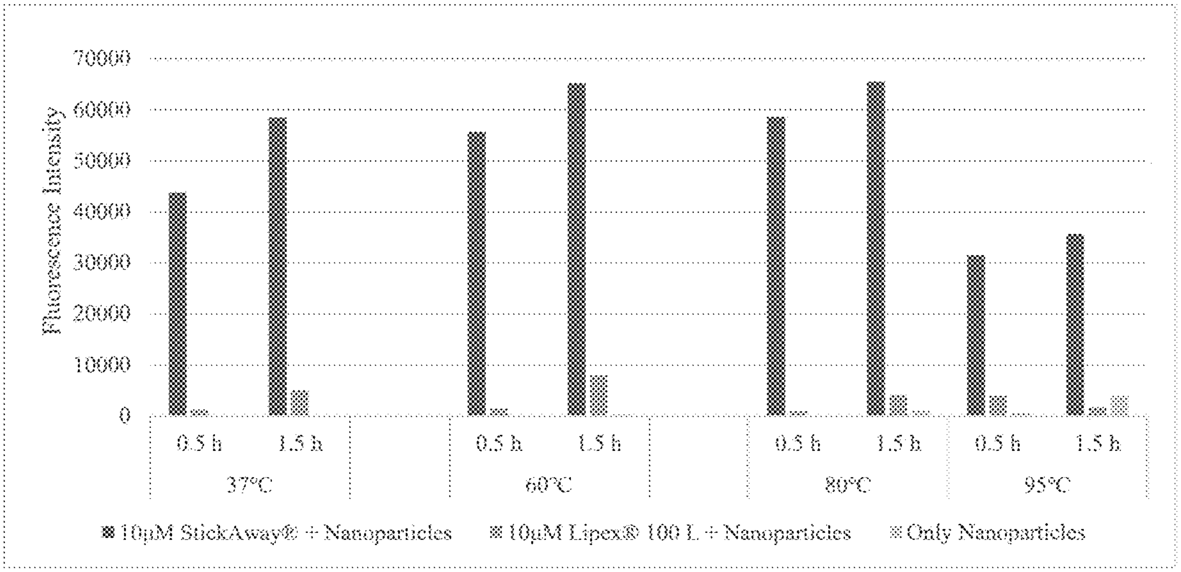
FIG. 5 shows fluorescence intensity after the reaction with different enzymes on prepared PET nanoparticles in 96-well microtiter plate

Two commercialized enzymes, StickAway® and Lipex® 100 L (StickAway® is a commercial PET-degrading enzyme from Novozymes; Lipex® 100 L is a commercial lipase from Novozymes which has lower activity then StickAway® on PET fiber) were firstly diluted at 10 μM using DI water. Then, 150 μL of StickAway® (10 μM), Lipex® 100 L (10 μM) and Tris-HCl buffer (pH 7.4) were separately added into Eppendorf tubes in triplicate. And 50 μL PET nanoparticle solution prepared in Example 2 was added into each Eppendorf tube. Then, all tubes were put in the Gene-Explorer Gradient Thermal Cycler (GE4852, bought from Hangzhou Bio-Gener Technology Co., Ltd.) with designed temperature (37° C., 60° C., 80° C.) for 2 hours. After incubated for 0.5 h and 1.5 h, 50 μL solution were transferred from each tube to a 96-well microtiter plate (flat bottom, black, Corning, USA), to be measured with the EnSpire® Multimode Plate reader (Ex=488 nm, Em=523 nm) (PerkinElmer, USA). The results were shown in FIG. 5. The group with StickAway® show quite higher signal than both the group of Lipex® 100 L and Tris-HCl buffer at 37° C., 60° C. and 80° C., which means the prepared nanoparticles could well differentiate PET degrading enzymes from other enzymes at broader temperature range.

Example 4: PET Nanoparticles for Strain Screening in 96-Well Microtiter Plate

*Thermobifida alba* could produce cutinase and degrade PET and the related gene has been cloned and characterized by Doris et al. (Biocatalysis and Biotransformation, January-February 2012, 30 (1): 2-9). Therefore, *T. alba* (provided by Novozymes, under a collaboration project with Prof. Li Wenjun from Yunnan University, isolated from several compost, soil and hot spring sediment samples) was chosen as a positive strain on PET hydrolysis while *E. coli* (*Escherichia coli* ATCC 25922, bought from FuXiang Bio) was adopted as a control.

Both strains were inoculated and cultured in LB medium in 250 ml flasks for 72 hours. Then, the broth of *T. alba* and *E. coli*, as well as Tris-HCl buffer (pH 7.4) were separately added into in a 96-well microtiter plate (flat bottom, black, Corning, USA). The volume was 50 μL for each well. And 50 μL PET nanoparticle solution prepared in Example 2 was added into each well. Every condition was in triplicate. Meanwhile, another 50 μL broth of *T. alba* and *E. coli* were added into other 3 wells separately without PET nanoparticles as blank control. The final volume of all wells was adjusted to 200 μL with Tris-HCl buffer (pH 7.4).

Figure 6:
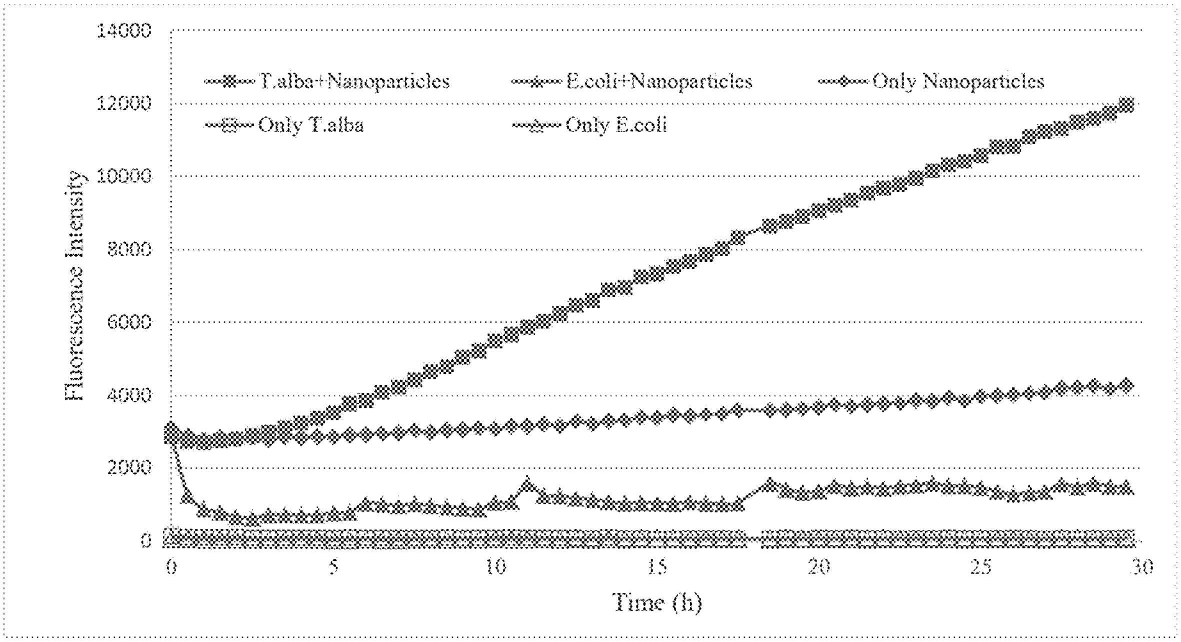
FIG. 6 shows fluorescence intensity after the reaction with different live cells on prepared PET nanoparticles in 96-well microtiter plate

Then the plate was measured by the EnSpire® Multimode Plate reader (PerkinElmer, USA) at 37° C. for 30 hours. The fluorescence intensity was measured every 30 min. As the results in FIG. 6, compared with *E. coli* and other blank groups, *T. alba* could produce PETase which could degrade PET nanoparticles and generate significantly higher fluorescence signal. It means the prepared PET nanoparticles could well differentiate live microbes which could produce PET degrading enzymes from other microbes in 96-well plate. In addition, the live microbes screening conducted in microtiter plate with nanoparticles has the advantages of high throughput.

Example 5: Fluorescence Activated Droplet Sorting (FADS) System

Microfluidic Device Fabrication

Microfluidic devices used for droplet generation, picoinjection, and sorting were fabricated in poly(dimethyl-siloxane) (PDMS) using rapid-prototyping soft lithography. The devices had channel heights between 14-25 μm and holes that were punched for channel inlets and outlets. The devices for picoinjection and sorting contained electrodes fabricated by filling empty channels in the shape of electrodes with low melting-temperature liquid solder (Indium Co., Clinton, NY, USA).

Optical Detection System

A home-made integrated optical system was designed. The system consisted of a compact optical module to measure the fluorescence of droplets, a high voltage module to deliver a high voltage-high frequency electric field to solder injected electrodes, a high-speed CCD camera to capture images and videos, and a power supply module to control the microscope and FADS system. The detection module (160 mm×143 mm×54 mm in size) contained a high-power diode laser, three photomultipliers (PMT) for detection of three fluorescence signals, and a 2 MHz analog-to-digital conversion circuit. The wavelength of the laser and detectors can be flexibly customized to enable simultaneous detection of multiple fluorogenic indicators. The V-mount of the detection module allowed easy connection with the side port of a standard inverted microscope. The optical path was aligned and die bonded in the detection module. This optical system is alignment-free and features a compact size, lightweight portability, quick installation, and high robustness. The FADS process was controlled using a program written in LabVIEW software (National Instruments, USA). Time series recordings were analyzed using a program written in Matlab (MathWorks, Natick, MA, USA) to extract the fluorescence signal of each droplet. Before and after sorting, droplets were collected and imaged by fluorescence microscopy (Eclipse Ti, Nikon, Tokyo, Japan).

Example 6: PET Nanoparticles for Enzyme Screening in FADS System

Figure 7:
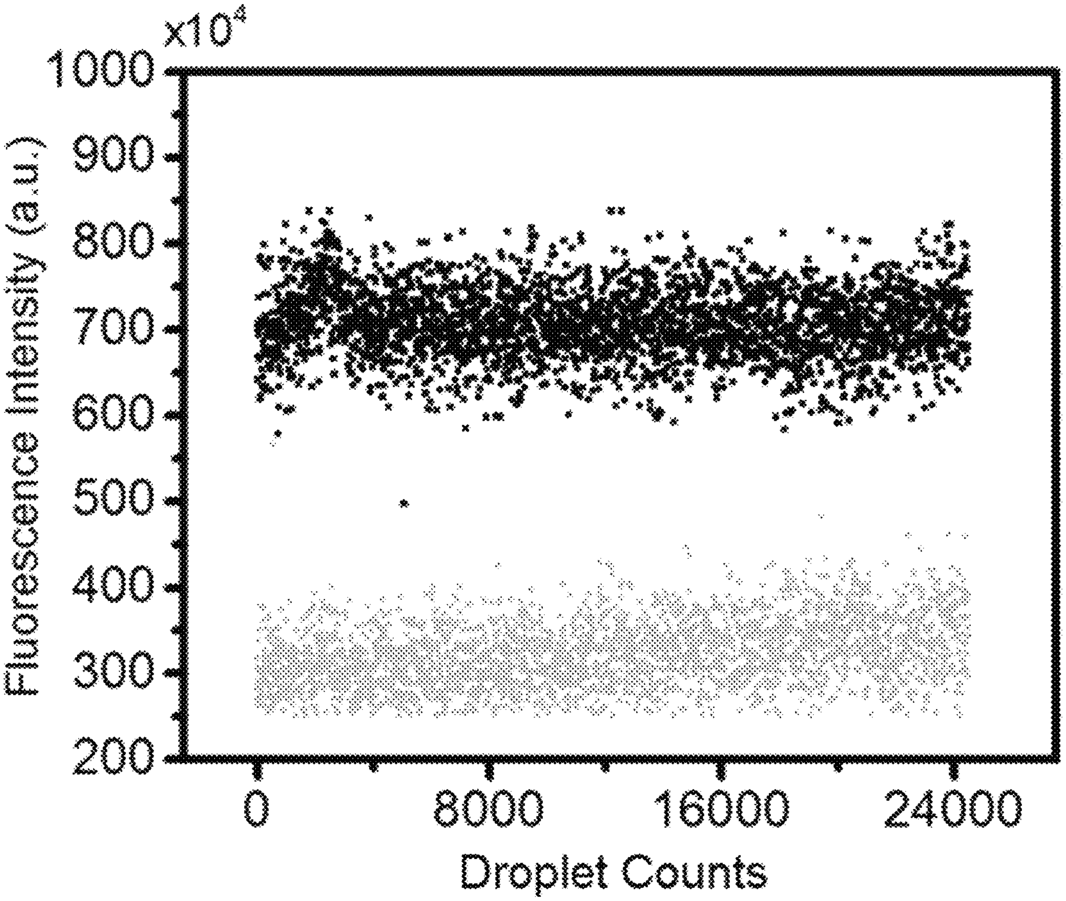
FIG. 7 shows fluorescence intensity after the reaction with different enzymes on PET nanoparticles in micro-droplets, wherein black dots: 10 μM StickAway®+Nanoparticles; grey dots: 10 μM Lipex® 100 L+Nanoparticles

Two commercialized enzymes, StickAway® and Lipex® 100 L (same with Example 3) were firstly diluted at 10 μM using 10 mM Tris-HCl buffer (pH=7.4). Microdroplets with active substances inside were generated using flow-focusing microfluidic device. Droplets with volumes about 3-4 μL were generated at a rate of 2700 per second. The device was operated with a total aqueous flow rate of 40 μL/h and 80 μL/h fluorinated oil with a surfactant (Cat. No. 186-4006, BioRad, Hercules, CA, USA). As described, two enzyme solutions were separately introduced to the flow focusing chip and generated droplets. The generated droplets were incubated in a 20-30 cm long piece of Teflon tubing (Cat. No. AWG30, 0.010 inch i.d., 0.028 inch o.d., Zeus Inc., Orangeburg, SC, USA), with both ends of the tubing sealed with capillary wax (Hampton Research, Aliso Viejo, CA, USA). The incubated droplets were re-loaded into the picoinjection device to introduce PET nanoparticles in Example 2. A voltage between 0 and 200 V at a frequency of 30 kHz was applied to the electrodes to trigger the injection at a throughput of 300 droplets per second. The droplets were collected in the receiving Teflon tubing (20-30 cm in length), then incubated. The Teflon tubing with droplets was connected to the sorting device with a channel depth of 25 μm. The sorting process was operated with a flow rate of 10 μL/h droplets and 100 μL/h fluorinated oil to space the droplets. The fluorescence signal of each droplet with both StickAway® and Lipex® 100 L were collected and mounted to the side port of the inverted microscope (IX81, Olympus, Japan). Based on the detected fluorescence intensity data in FIG. 7, it is easy to sort out the StickAway® droplets from the Lipex® 100 L droplets with a threshold set at 500 a.u. It is indicated that the prepared PET nanoparticles in Example 2 could be used to screen PET-degrading enzymes using FADS system, which is known as an ultra-high-throughput screening system.

Example 7: PET Nanoparticles for Strain Screening in FADS System

The culture broth of *T. alba* and *E. coli* in Example 4 were adjusted to approximately $7\times10^7$ cells/mL using culture medium. Then the cell suspensions were separately introduced into the flow-focusing chip under the same operating conditions in Example 6. And the theoretical concentration of the droplet system is about 0.3 cell/droplet, resulting in approximately 74.1% of droplets empty and 22.2% droplets containing a single cell. The generated droplets were incubated in a 20-30 cm long Teflon tubing (ID: AWG30, 0.010-inch i.d., 0.028-inch o.d., Zeus Inc., Orangeburg, SC, USA) at 37° C. for 1-2 d, with both end of the tubing sealed with capillary wax (Hampton Research, Aliso Viejo, CA, USA), to allow accumulation of sufficient enzymes from those microbial cells. The droplets were subsequently loaded into the picoinjection device (0-200V, 30 kHz) to introduce PET nanoparticles prepared in Example 2 as fluorogenic substrate. The droplets were collected in the receiving Teflon tubing (20-30 cm in length) and incubated at room temperature for 2 h.

Figure 8:
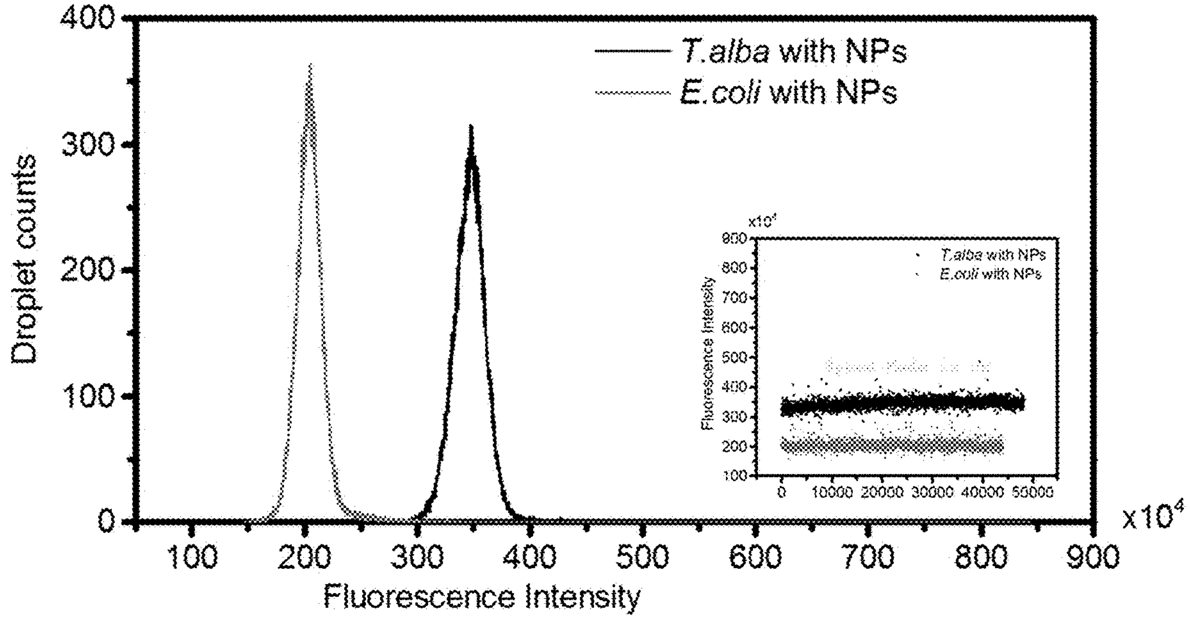
FIG. 8 shows fluorescence intensity after the reaction with live microbial cells on PET nanoparticles in micro-droplets; NPs was short name of nanoparticles

Afterwards, the droplets with microbial cells inside were injected into the sorting device. The flow rate of droplet suspension is 10 μL/h while fluorinated oil was operated at 100 μL/h to space the droplets. The fluorescence signal of each droplet with both *T. alba* and *E. coli* cells was collected and mounted to the side port of the inverted microscope (IX81, Olympus, Japan). Based on the detected fluorescence intensity data in FIG. 8, it is easy to sort out the *T. alba* droplets from the *E. coli* droplets with a threshold set at $280\times10^4$ a.u. The results indicate that the prepared PET nanoparticles in Example 2 can be used to screen PET-degrading microbes using FADS system, which is known as an ultrahigh-throughput screening system.

Figure 9:
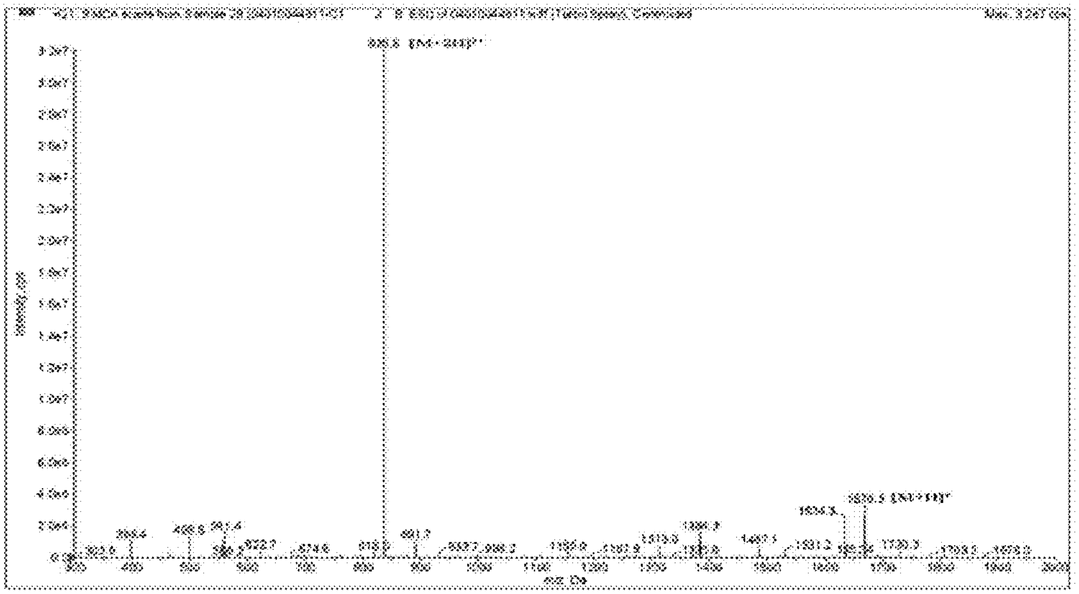
FIG. 9 shows the MS spectrum of FRET peptide indicator

Example 8: Synthesis of Fluorescence Resonance Energy Transfer (FRET) Peptide Indicator Fluorescence Resonance Energy Transfer (FRET) peptide is a pair of fluorescent indicators placed in close proximity, which is widely used for the detection of protease activity. It comprises of a specific peptide with a sequence of SHLVEALYK, and 6-carboxyfluorescein (6-FAM) at the N-terminus as the fluorescent donor (Ex=495 nm and Em=520 nm), and DABCYL at the C-terminus as the quencher. Quenching of the 6-FAM by distance-dependent resonance energy transfer to the DABCYL quencher is eliminated upon cleavage of the intervening peptide linker by protease, the fluorescence can be detected at a wavelength of 520 nm. The FRET peptide indicator was commercially synthesized by China Peptides (Shanghai, China). It was synthesized by Fmoc solid-phase synthesis on resin. The mixture was purified by reversed phase-high-performance liquid chromatography (RP-HPLC), eluting with a 40-70% gradient of acetonitrile in water. The target product was isolated with a purity of 96.7% and characterized by mass spectrometry (MS) spectrum to confirm the structure. FIG. 9 shows the MS spectrum of FRET peptide, which has a molecular weight of 1668.86 g/mol.

Example 9: Preparation of Wool Nanoparticles with FRET Peptide Indicator

Wool fiber (available from Jiaxing Jiashi Trading Co., Ltd. Zhejiang, China) was firstly solubilized by imidazolium ionic liquid (IL). 1-Butyl-3-methylimidazolium chloride ([Bmim]Cl, Aladdin, Shanghai, China) is one of the imidazolium ILs. 10 g [Bmim]Cl was heated to 120° C. by oil bath. Wool fibers were immersed in [Bmim]Cl at a weight ratio of 1:10, and the solution was mechanically stirred for 30 min. Dimethyl sulfoxide (DMSO, Xilong Scientific Co., Ltd. Guangdong, China) was added to the wool/IL solutions to reduce the solution viscosity. Then, 1 mg FRET indicator dissolved in DMSO (1 mg/mL) was added to the wool fiber/IL/DMSO solution under stirring at 200 rpm. Excess ethanol was loaded in 50 mL plastic syringe, and then added at the rate of 1 mL/min using the syringe pump (Longer Pump, Hebei, China) to the wool/IL/DMSO solution to precipitate wool nanoparticles under permanent stirring at room temperature. After desolvation treatment, 0.4 mL of glutaraldehyde (8% aqueous solution, Sinopharm Chemical Reagent Co., Ltd. Shanghai, China) was added for nanoparticles stabilization by cross-linking. Nanoparticles were stirred for 24 h and then separated by centrifugation for 5 min at 10,000 rpm and washed thoroughly with $ddH_2O$ to remove ethanol, excess of glutaraldehyde for several cycles. At each cycle, nanoparticles were resuspended in $ddH_2O$. Then the nanoparticle suspension was ready for use.

Figure 10:
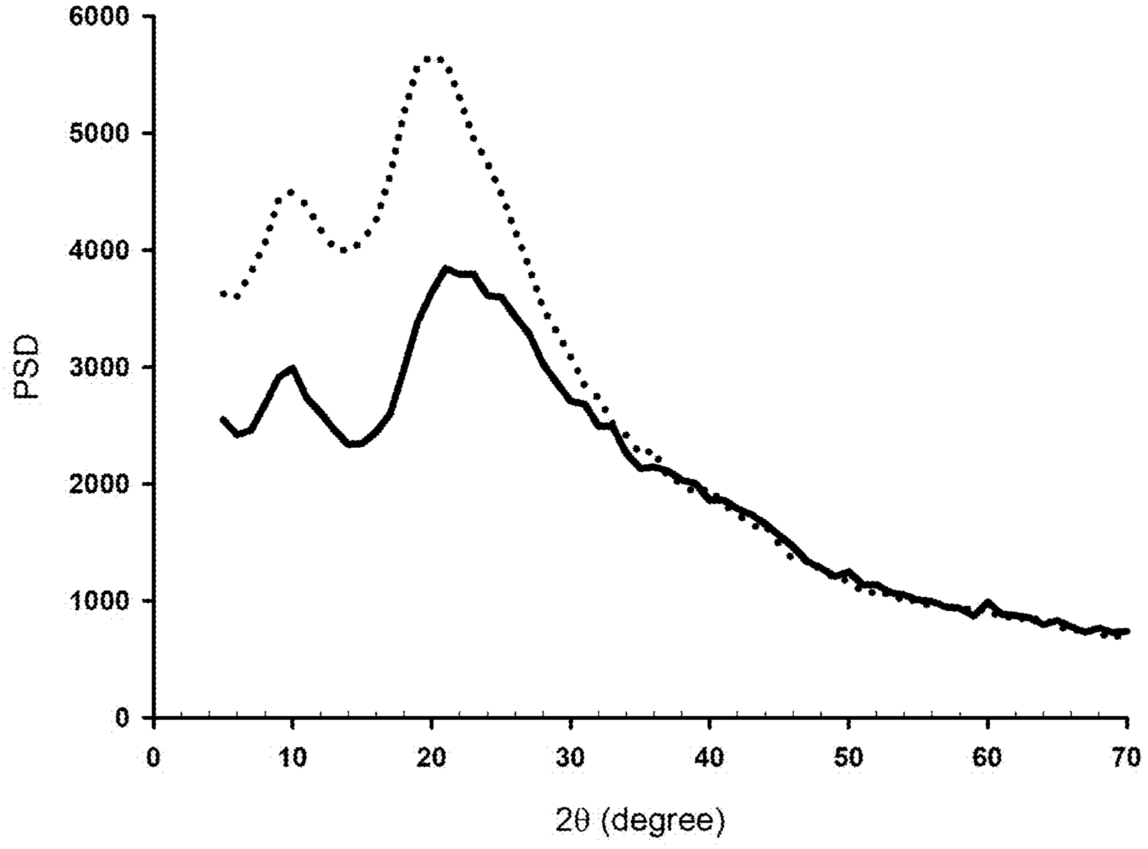
FIG. 10 shows the X-ray Diffraction (XDR) of wool and prepared wool nanoparticles, wherein solid line: wool; dotted line: wool nanoparticles

The hydrodynamic diameter of the nanoparticles in aqueous solution (0.5 mg/mL) were determined by dynamic light scattering (DSL) using a Zetasizer Nano ZS90 (Malvern Panalytical Ltd., UK) at 25° C. The obtained nanoparticles have an average diameter of 315.3 nm. Wool fiber has crystal structure which is a key property for the degradation by bioactive substance because the crystal structure will influence the accessibility of the targeting cleavage sites. Therefore, prepared wool nanoparticles were measured by X-ray Diffraction (XRD) on Rigaku SmartLab X-ray diffractometer (Rigaku, USA) within the 29 angle range from 5° to 70° for crystal structure analysis. FIG. 10 shows XRD patterns for wool and wool nanoparticles. Both materials exhibit two peaks at 29 of about 10° and 20° which indicates that wool fiber and prepared wool nanoparticles have the same crystal form. The retaining crystal structure in nanoparticles is important to ensure a good correlation of prepared nanoparticles to original fiber in application.

Figure 11:
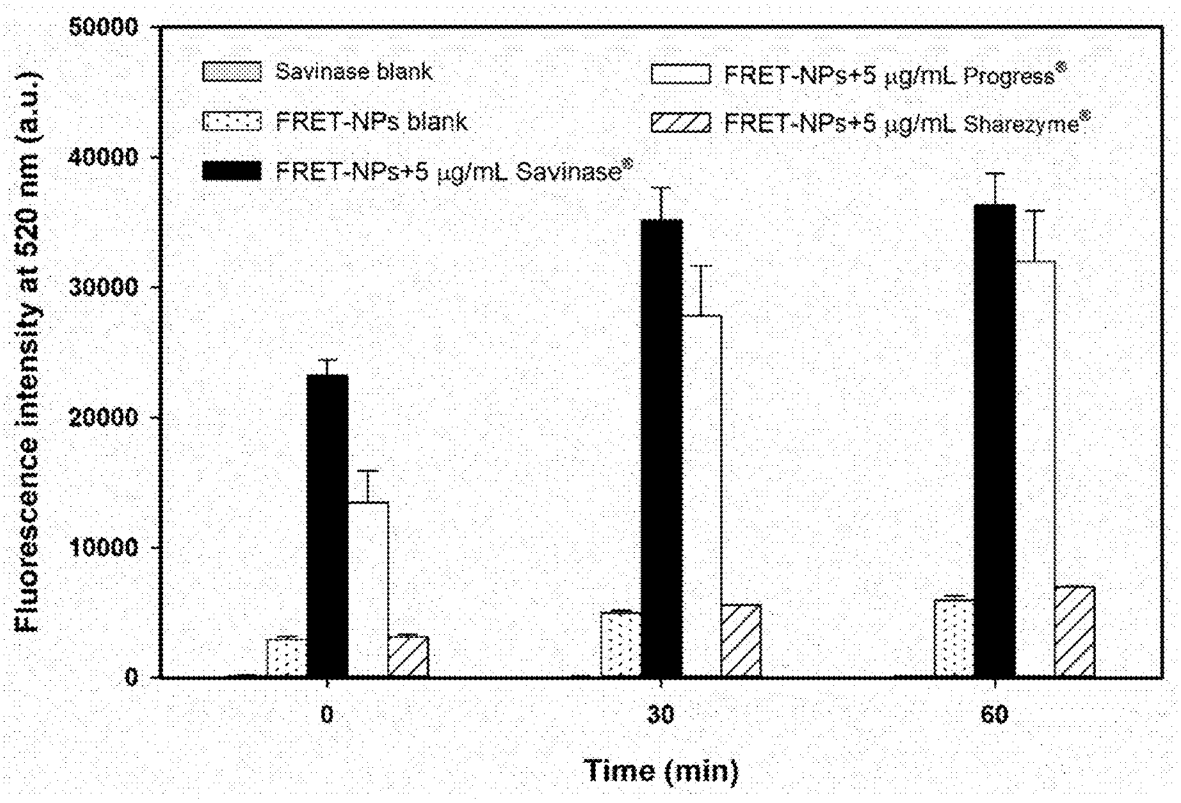
FIG. 11 shows the fluorescence intensity after the reaction with different enzymes on prepared wool nanoparticles in 96-well microtiter plate; NPs was short name of nanoparticles

Example 10: Enzyme Screening by Wool Nanoparticles with FRET Indicator in 96-Well Microtiter Plate Enzymatic hydrolysis of wool nanoparticles was carried out in 96-well microplates (Corning, Inc., USA). Reactions were performed at 50° C. in 200 μL system, which contained 50 mM Glycine-NaOH buffer (pH 9.5), 1 mg/mL wool nanoparticles prepared in Example 9 and 5 μg/mL different enzymes (Savinase®, Progress®, Sharezyme®, all provided by Novozymes). The enzyme reaction was measured by monitoring the increase of fluorescence intensity (Ex=495 nm, Em=520 nm) using the EnSpire® Multimode Plate reader (PerkinElmer, USA). Activity of these three enzymes on wool was determined by the detection of amino acid releasement after enzyme hydrolysis at pH 9.5 and 50° C. From detection, Savinase® had higher enzyme activity than Progress® on wool. Sharezyme® (with main activity of xylanase) didn't have activity on wool. FIG. 11 shows the fluorescence intensity after the reaction with different enzymes on prepared wool nanoparticles, and the results indicate that the prepared wool nanoparticles can well differentiate wool degrading enzymes from other enzymes, as well as different enzyme activities on wool. Prepared wool nanoparticles can be used in the high throughput screening for enzyme library which contains different enzymes or enzyme variants with different activities.

Figure 12:
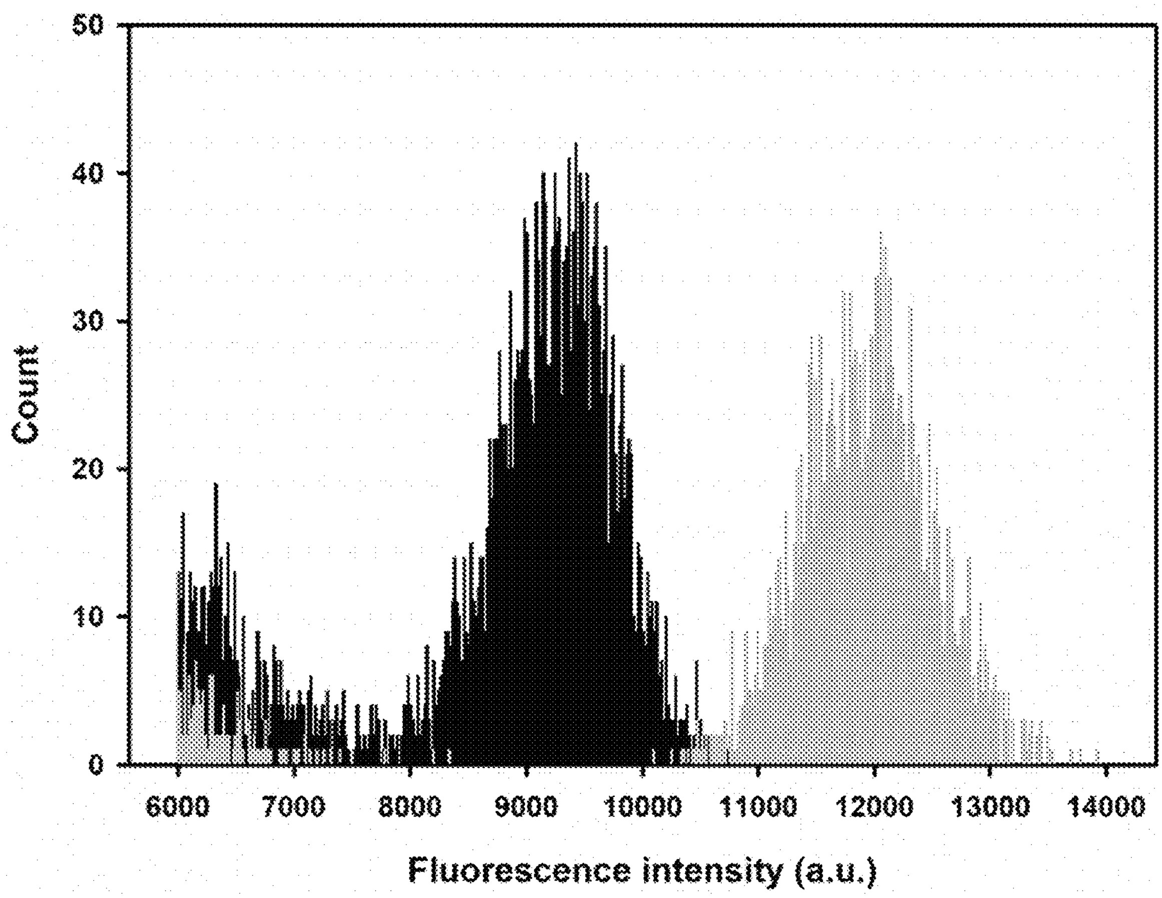
FIG. 12 shows fluorescence intensity after the reaction with wool degrading enzyme on prepared wool nanoparticles in micro-droplets, wherein grey dots: Savinase®+ Nanoparticles; black dots: Nanoparticles alone

Example 11: Enzyme Screening by Wool Nanoparticles with FRET Indicator in FADS System Enzyme reactions were performed firstly at 50° C. in 200 μL system, which contained 50 mM Glycine-NaOH buffer (pH 9.5), 1 mg/mL wool nanoparticles prepared in Example 9 and 0 or 5 μg/mL Savinase®. After 2 hours' reaction, the solutions were introduced to the flow focusing microfluidic device and generated 50 μL droplets as described in Example 5. The device was operated with a total aqueous flow rate of 20 μL/h and 450 μL/h fluorinated oil with a surfactant (Cat #186-4006, Bio-Rad, Hercules, CA, USA). The fluorescence signals of each droplets with and without Savinase® were respectively collected using the custom-made compact detection module mounted to the side port of an inverted microscope (IX81, Olympus, Japan). Based on the detected fluorescence intensity data in FIG. 12, it is easy to sort out the Savinase® droplets from the buffer droplets by defining the fluorescence threshold at 11000. is the results indicate that the wool nanoparticles prepared in Example 9 can be used to detect wool-degrading enzymes using FADS system.

Example 12: Preparation of Wool Nanoparticles with FITC Indicator

In Example 9, the FRET peptide indicator involves electron energy transfer between two different fluorophores, and indicator does not emit fluorescence until digested by specific enzymes. In this example, Fluorescein isothiocyanate, Isomer I (FITC, F104848, Aladdin, Shanghai, Chinaa bright green fluorophore under excitation) was heavily encapsulated as indicator. The FRET events occur as a result of fluorescence homotransfer in which fluorescein is acting both as the energy “donor” and energy “acceptor”. The degradation of nanoparticles could result in the decrease in fluorescence quenching, namely the increased of fluorescence.

For nanoparticles preparation, wool fiber (available from Jiaxing Jiashi Trading Co., Ltd. Zhejiang, China) was firstly solubilized by IL of [Bmim]Cl as described in Example 9. It was divided into two parts, one was kept in the incubator at 70° C. Fluorescein isothiocyanate, Isomer I (FITC, F104848, Aladdin, Shanghai, China) was dispersed in DMSO (Xilong Scientific Co., Ltd. Guangdong, China), and then added to another wool/IL solution. The reaction mixture was stirred in the dark at room temperature for 24 h. The FITC conjugated wool (FITC-wool) in IL solution were then added to the other wool/IL solution at a weight ratio of 1:2. Excess ethanol was added dropwise at room temperature under continuously stirring to precipitate FITC-wool encapsulated wool nanoparticles. Nanoparticles were stirred for 24 h and then separated by centrifugation for 5 min at 10,000 rpm and washed thoroughly with $ddH_2O$ to remove ethanol and free FITC-wool for several cycles. At each cycle, nanoparticles were resuspended in $ddH_2O$. Then the hydrodynamic diameter of the FITC-wool nanoparticles in aqueous solution (0.5 mg/mL) were determined by DSL using a Zetasizer Nano ZS90 (Malvern Panalytical Ltd., UK) at 25° C. The obtained nanoparticles have an average diameter of 260 nm.

Figure 13:
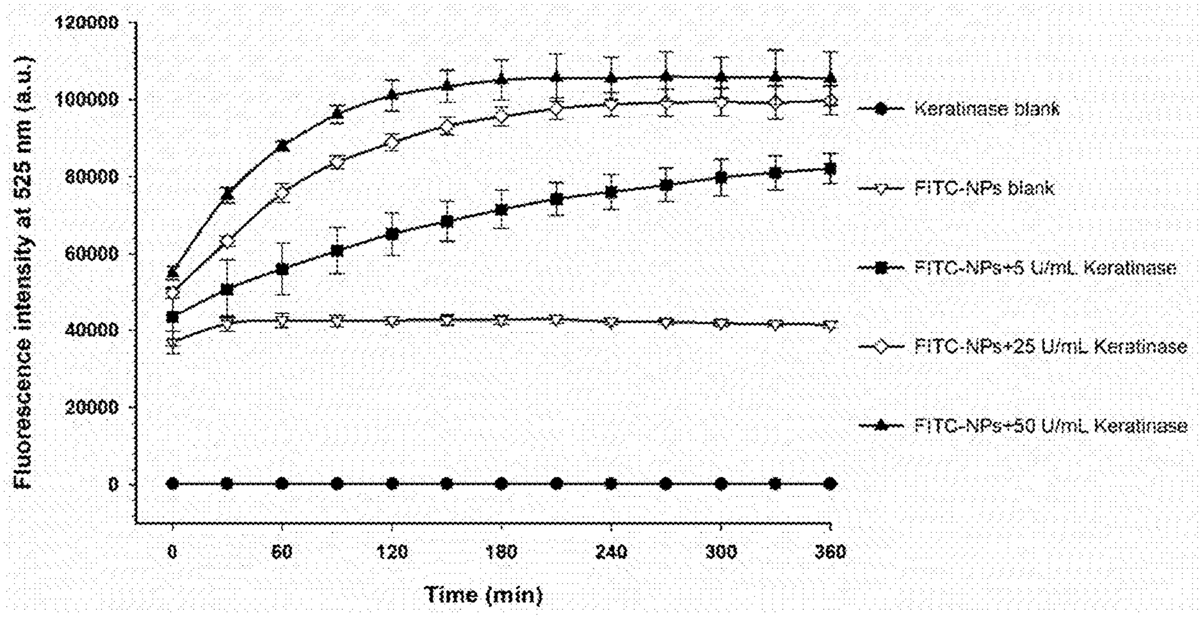
FIG. 13 shows the fluorescence intensity after the reaction with wool degrading enzyme on prepared wool nanoparticles (FITC indicator) in 96-well microtiter plate; NPs was short name of nanoparticles

Example 13: Wool Nanoparticles with FITC Indicator for Enzyme Screening in 96-Well Microtiter Plate Enzyme hydrolysis of wool nanoparticles was carried out in 96-well microplates (Corning, Inc., USA). The reactions were performed at 50° C. in 200 μL system, which contained 50 mM Glycine-NaOH buffer (pH 10.5), 1 mg/mL wool nanoparticles prepared in Example 12, and 5-50 U/mL commercial keratinase (available from Shanghai yuanye Bio-Technology Co., Ltd., Shanghai, China). The enzyme reactions were monitored by the increase of fluorescence intensity (Ex=495 nm, Em=520 nm) using the EnSpire® Multimode Plate reader (PerkinElmer, USA). FIG. 13 shows the fluorescence intensity after the hydrolysis of keratinase with different activity on FITC-nanoparticles. From the results, the fluorescence intensity increased with the increasing of enzyme activity, which indicates that the prepared wool nanoparticles can well differentiate wool degrading enzymes which have different activity. Prepared wool nanoparticles can also be used in the high throughput screening for the enzyme library which contains enzyme variants with different activities.

Example 14 Preparation of Retrograded Starch Nanoparticles

Firstly, 0.25 g corn starch (9005-25-8, Aladdin, Shanghai, China) was dissolved in 20 mL DI water (Milli-Q) and gelatinized by 150° C. oil bath (HWCL-3, Greatwall, Zhengzhou, China) for 30 min. Then, 25 μL 10 mg/mL DQ-starch indicator (EnzChek® Ultra Amylase Assay Kit, E33651, Molecular Probes, Inc.) was added and mixed. The indicator can be hydrolyzed by amylase to produce fluorescence and achieve the purpose of fluorescence detection. Then, the solution was cooled at room temperature. Then install the plug back and remove bubble in the syringe and get Teflon tubing (i.d. 0.5 mm, o.d. 0.9 mm, from Zeus) connected with its needle. Afterward, adjusting the stirring speed to 400 rpm, and dropwise ethanol to the solution until 75 mL using a syringe pump (Longerpump, Hebei, China). Retrograded starch nanoparticles formed in the solution when the solution was left overnight at room temperature and stirring. Eluting the retrograded starch nanoparticles three times with ethanol to remove excess and free DQ-starch indicator by centrifugation (Centrifuge 5418 R, Eppendorf Eppendorf). Then the mixture was centrifugated at 6000 rpm, 4° C., 10 min on a centrifugal machine (Centrifuge 5418 R, Eppendorf). Then retrograded starch nanoparticles were lyophilized for use.

Figure 14:
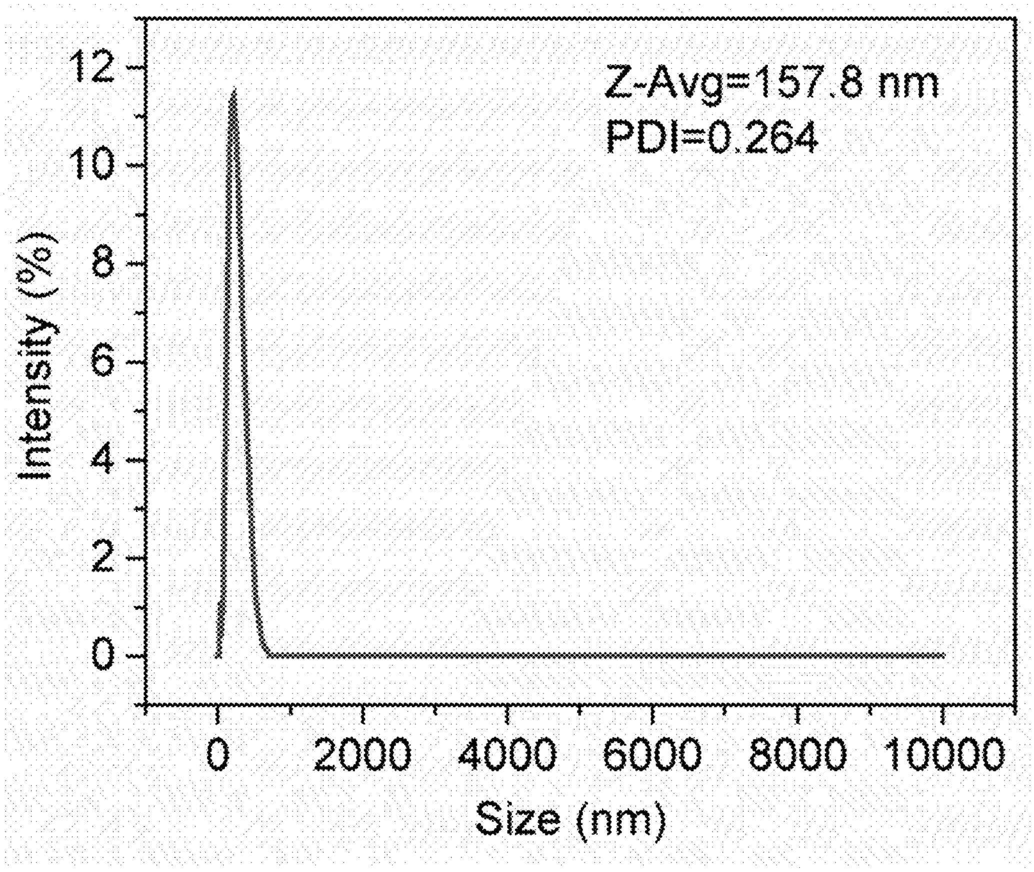
FIG. 14 shows the Dynamic Light Scattering (DLS) of prepared retrograded starch nanoparticles
Figure 15:
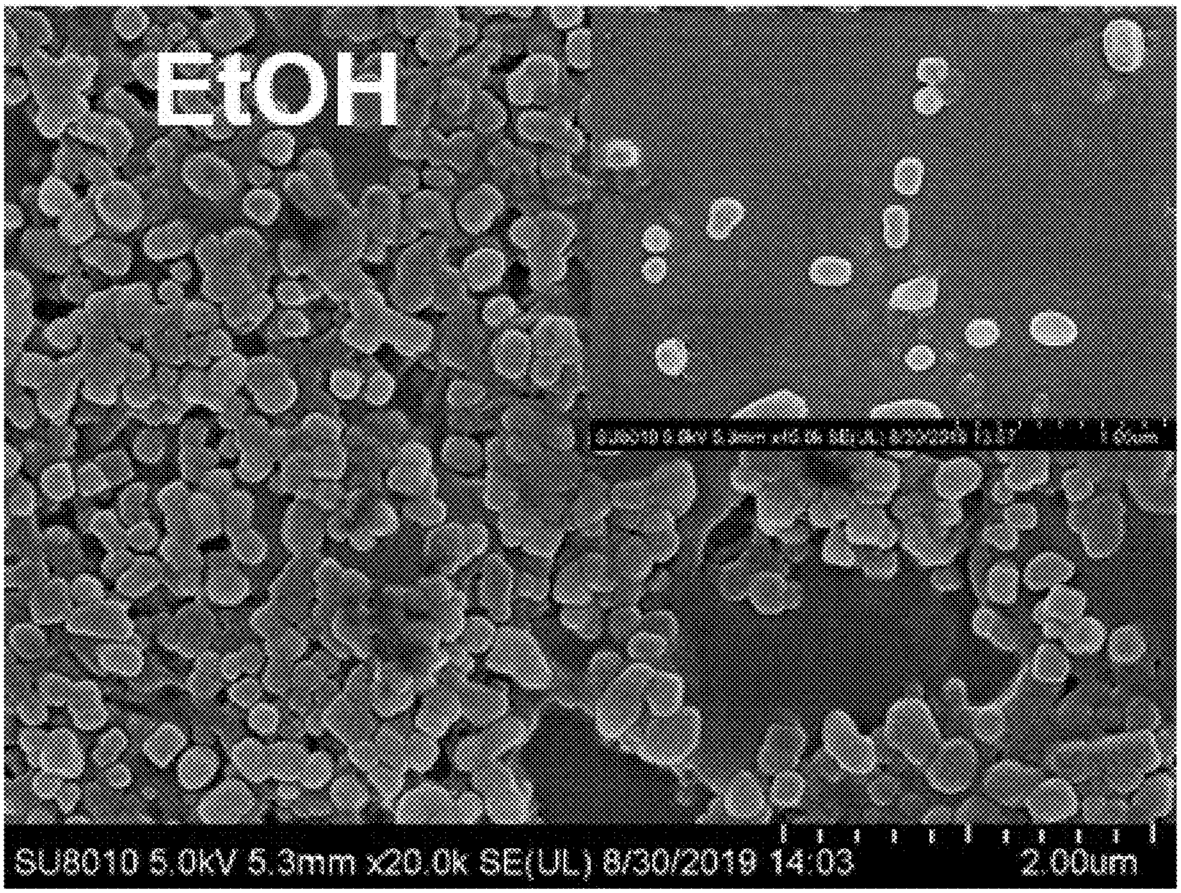
FIG. 15 shows the scanning electron microscope (SEM) of prepared retrograded starch nanoparticles

The obtained retrograded starch nanoparticles were characterized using Dynamic Light Scattering (DLS, Zetasizer Nano-ZS 90, Malvern Instruments), which shows an average diameter of 157.8 nm and Polydispersity index (PDI) of 0.264 (FIG. 14). The surface morphologies of nanoparticles were examined under vacuum with a JSM-7100F thermal field emission scanning electron microscope (SEM, JEOL Ltd. Japan) with the results are shown in FIG. 15. All the nanoparticles exhibit irregular spherical orellipsoidal shapes. The encapsulated DQ-starch indicator was about 0.25% (w/w) in nanoparticles. This value was obtained by the determination of fluorescence intensity releasement of pre-unit mass DQ-starch indicator and per-unit mass nanoparticles after hydrolysis with overdosed enzymes. Specifically, 1 μg DQ-starch substrate released the fluorescence intensity of 23430 relative fluorescence unit (RFU). For prepared retrograded starch nanoparticles, 100 μg Nanoparticles released the fluorescence intensity of about 6000 RFU, and this value was equivalent to the fluorescence releasement from 0.25 μg DQ-starch.

Figure 16:
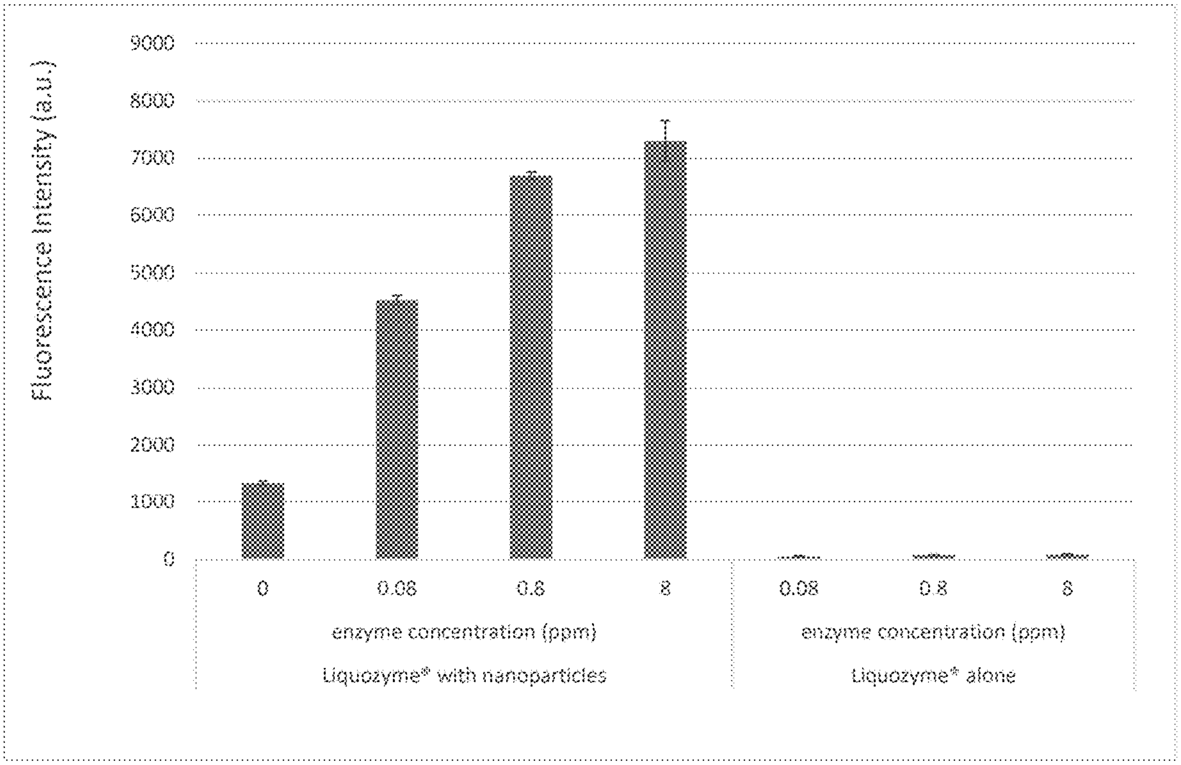
FIG. 16 shows fluorescence intensity after the reaction with retrograded starch degrading enzyme on prepared retrograded starch nanoparticles in 96-well microtiter plate.

Example 15: Retrograded Starch Nanoparticles for Amylase Detection in 96-Well Microtiter Plate Liquozyme® is a commercial amylase provided by Novozymes which could react on retrograded starch. Liquozyme® was firstly diluted from 100,000 to 100 times using 40 mM Ammonium bicarbonate buffer (pH 9.5). Then, 100 μL amylase solution and 100 μL retrograded starch nanoparticles prepared in Example 14 were added into a 96-well microtiter plate (flat bottom, black, Corning, USA) to get final concentration of 0.08-8 ppm enzyme and 0.5 mg/mL nanoparticles in 200 μL reaction system. Then, the plate was put in the EnSpire® Multimode Plate reader (Ex=502 nm, Em=517 nm) (PerkinElmer, USA) at 37° C. for 20 min. After incubation, every well was measured for detecting the fluorescence intensity. As shown in FIG. 16, the fluorescence intensity increased with the increasing of enzyme concentration, which indicated that the prepared retrograded starch nanoparticles could well differentiate different amylase activity by fluorescence signal.

Figure 17:
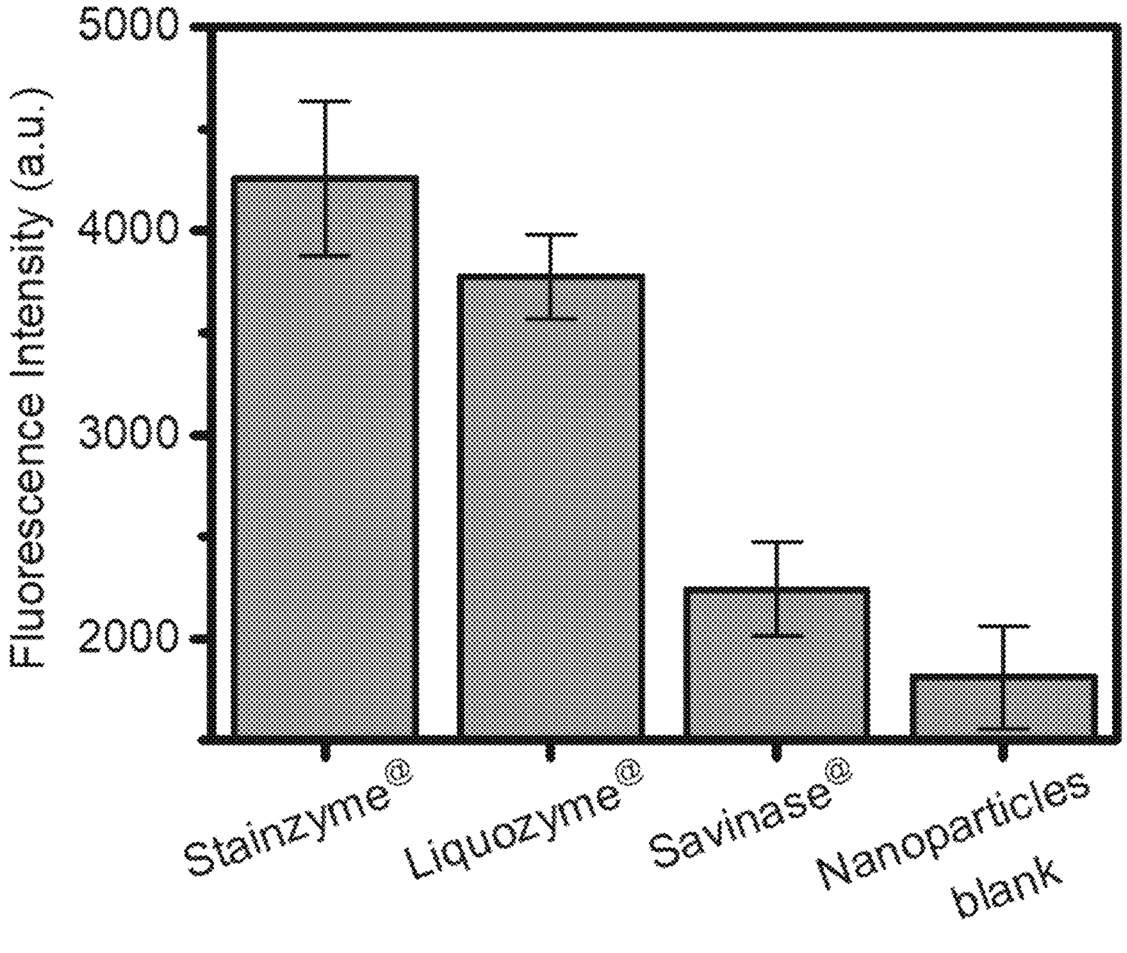
FIG. 17 shows fluorescent intensity after the reaction with different enzymes on prepared retrograded starch nanoparticles in 96-well microtiter plate

Example 16: Retrograded Starch Nanoparticles for Enzyme Screening in 96-Well Microtiter Plate Enzyme hydrolysis of retrograded nanoparticles was carried out in 96-well microplates (polystyrene black flat 96-well no. 3925; Corning, Inc., USA). Reactions were performed in 200 μL system at 37° C., which contained 20 mM $NaHCO_3$—NaOH buffer (pH 9.5), 0.5 mg/mL nanoparticles prepared in Example 14, and 25 ng/mL different enzymes (Stainzyme®, Liquozyme®, Savinase®, all provided by Novozymes). The enzyme reaction was measured by monitoring the increase of fluorescence intensity (Ex=502 nm, Em=517 nm) after 1-hour reaction using the EnSpire® Multimode Plate reader (PerkinElmer, USA). Enzyme activity on retrograded starch was determined by the detection of reducing sugar releasement after enzyme hydrolysis at pH 9.5 under 37° C. Here, retrograded starch was made from the same corn starch as Example 14. 1 L corn starch suspensions was prepared firstly by putting 75 g starch into 1 L DI water (Milli-Q). Then the prepared starch suspensions were put into 2 L boiling water and boiled for 10 minutes with stirring constantly. Then the system cooled down to 25° C., and retrograded starch was generated for use. Through enzyme activity detection, Stainzyme® had higher enzyme activity than Liquozyme® on retrograded starch. Savinase® (with the main activity of protease) didn't have activity on retrograded starch. FIG. 17 showed the fluorescence intensity after the reaction with different enzymes on prepared retrograded starch nanoparticles, and the results indicate that the prepared retrograded starch nanoparticles can well differentiate retrograded starch degrading enzymes from other enzymes, as well as different enzyme activities on retrograded starch. Prepared retrograded starch nanoparticles can also be used in the high throughput screening for enzyme library which contains different enzymes or enzyme variants with different activities.

Figure 18:
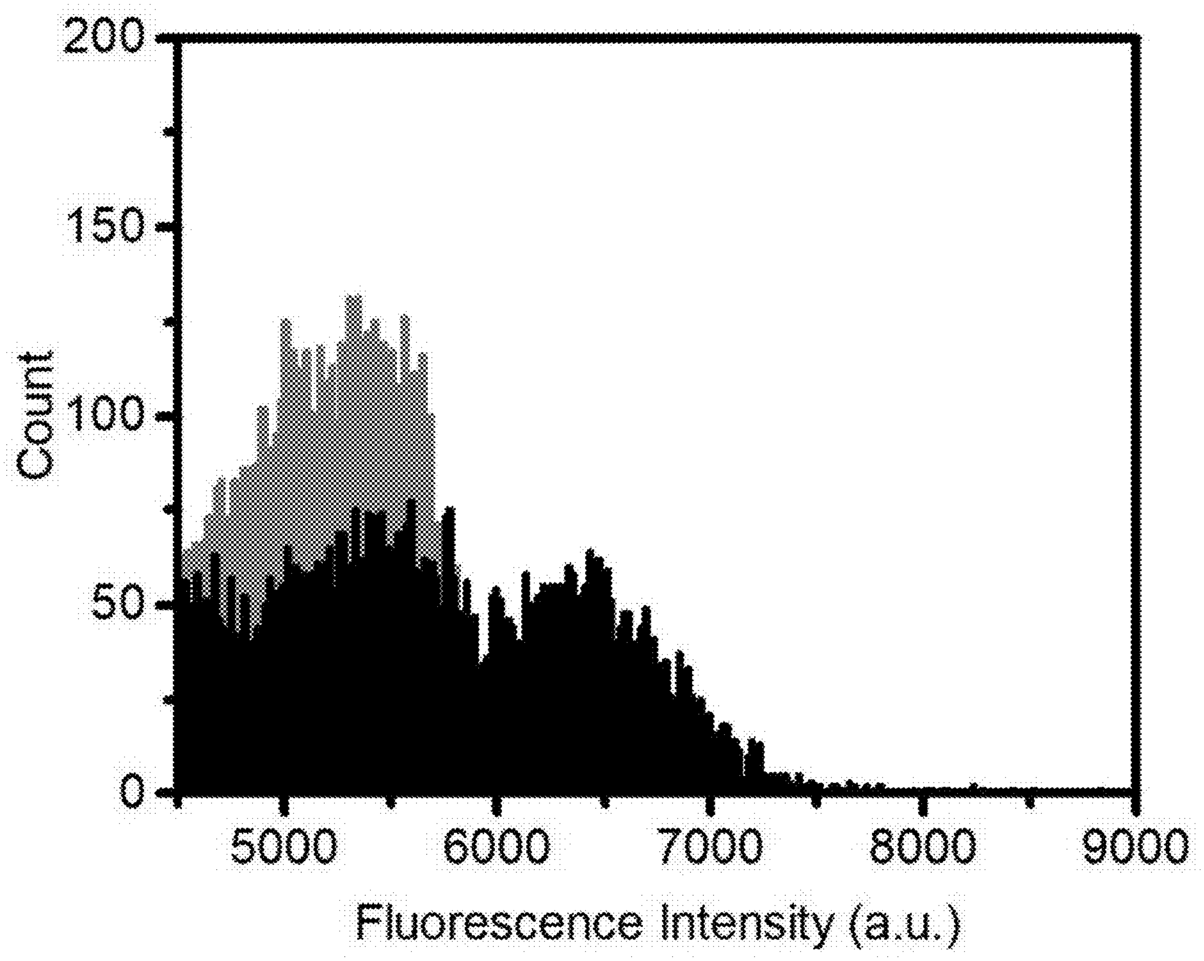
FIG. 18 shows fluorescence intensity after the reaction with amylase on prepared retrograded starch nanoparticles in micro-droplets, wherein black dots: Liquozyme®+Nanoparticles; grey dots: Nanoparticles alone

Example 17: Retrograded Starch Nanoparticles for Enzyme Screening by FADS System To evaluate if the retrograded starch nanoparticles can serve as the indicator for droplet sorting of retrograded starch degrading enzymes, we choose the commercialized enzyme, Liquozyme® (same with Example 15) to make the positive droplet with retrograded starch nanoparticles. Liquozyme® was firstly diluted at 10 μM. The retrograded starch nanoparticles prepared in Example 14 was 1 mg/mL. Microdroplets with active substances inside were generated using flow-focusing microfluidic device. Droplets with volumes about 20 μL were generated. The device was operated with a total aqueous flow rate of 40 μL/h and 450 μL/h fluorinated oil with a surfactant (Cat. No. 186-4006, BioRad, Hercules, CA, USA). The negative droplets contained retrograded starch nanoparticles solution, but without enzyme. The negative droplets were generated using the same flow-focusing microfluidic device. The generated droplets were incubated in a 20-30 cm long piece of Teflon tubing (Cat. No. AWG30, 0.010-inch i.d., 0.028-inch o.d., Zeus Inc., Orangeburg, SC, USA), with both ends of the tubing sealed with capillary wax (Hampton Research, Aliso Viejo, CA, USA). The incubated droplets were re-loaded into the sorting device to measure the fluorescence intensity. Based on the detected fluorescence intensity data in FIG. 18, droplets with Liquozyme® could be sorted out from the droplets without enzyme reaction by a threshold set. The results indicate that the retrograded starch nanoparticles prepared in Example 14 could be used to detect retrograded starch-degrading enzymes using FADS system, and the prepared retrograded starch nanoparticles can be used in the ultrahigh throughput screening.

What is claimed is:

1. A method for screening a bioactive substance of a library which is capable of degrading or assisting in degrading a water-insoluble polymer matrix using a microfluidic-based system, said method comprising:

a) generating a first droplet containing a bioactive substance;

b) coalescing a secondary droplet containing a nanoparticle with the droplet generated in step a);

wherein the nanoparticle comprises water-insoluble polymer matrix encapsulating an indicator constituent, and wherein the indicator constituent is released from the nanoparticle only when the polymer matrix is degraded or broken; and wherein the nanoparticle is formed by providing a solution comprising one or more polymers, and then contacting the solution with a polymer non-solvent to produce the nanoparticle;

c) sorting the droplets in step b) based on an indicative effect generated by the indicator constituent, and d) analyzing the sorted droplets to screen for the bioactive substance;

wherein the bioactive substance is a water-insoluble polymer degrading enzyme or a water-insoluble polymer degrading microorganism.

2. The screening method according to claim 1, wherein, when the indicative effect of a droplet reaches or is above a preset threshold level, the droplet is selected.

3. The screening method according to claim 1, wherein the droplet sorting is based on a fluorescence activated droplet sorting technique.

4. The screening method according to claim 1, wherein water-insoluble polymer degrading enzyme is a hydrolase, isomerase, ligase, lyase, oxidoreductase, or transferase.

5. The screening method according to claim 1, further comprises a droplet incubation process, wherein the droplet containing the bioactive substance is incubated.

6. The screening method according to claim 1, wherein each droplet before sorting comprises at most a single cell.

7. The screening method according to claim 1, wherein the library is a microorganism library comprising a multitude of different microorganism, wherein the amount of indicative effect released by microorganism reaches or is above the predetermined threshold level, whereby a targeted enzyme or a targeted microorganism is identified.

8. The screening method according to claim 1, wherein the bioactive substance library is an enzyme library comprising a multitude of enzyme variants derived from a parent enzyme, wherein an increased amount of indicative effect has been released by the active enzyme variant, as compared with the parent enzyme, whereby an improved enzyme variant is identified.

9. The screening method according to claim 1, wherein the water-insoluble polymer matrix is degraded or broken, from which the indicator constituent is released, and then an indicative effect is triggered or enhanced.

10. The screening method according to claim 1, wherein the water-insoluble polymer matrix comprises or consists of an enzyme substrate.

11. The screening method according to claim 1, wherein the water-insoluble polymer is polyester, starch, saccharides, lipids, lignin, protein, nucleic acid, amylose, cellulose, pectin, chitin, fatty acids, lignin, alginate acid, hyaluronic acid, agar, mannan, xanthan gum, arabic gum, protein, DNA or RNA.

12. The screening method according to claim 1, wherein the water-insoluble polymer is polybutylene terephthalate (PBT), polypropylene terephthalate (PTT), polyethylene terephthalate (PEN), polyethylene terephthalate, tetramethylene terephthalate (PTMT), polyethylene-4-oxybenzoate, polyethylene glycol, polyvinyl chloride, polyglycolic acid, polylactic acid, polyanhydride, polycaprolactone, polyacrylonitrile, polypropylene, or polyvinyl alcohol.

13. The screening method according to claim 1, wherein the indicator constituent is a fluorogenic indicator.

14. The screening method according to claim 1, wherein both the polymer matrix and indicator constituent can be degraded or hydrolyzed by a specific active enzyme, and then, the indicative effect is triggered or enhanced.

* * * * *